(12) United States Patent
Blizzard et al.

(10) Patent No.: US 6,838,584 B2
(45) Date of Patent: Jan. 4, 2005

(54) ESTROGEN RECEPTOR MODULATORS

(75) Inventors: Timothy Allen Blizzard, Middletown, NJ (US); Milton Lloyd Hammond, Somerville, NJ (US); Jerry Dwain Morgan, Sayreville, NJ (US); Ralph Troy Mosley, Roselle, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/475,079

(22) PCT Filed: May 6, 2002

(86) PCT No.: PCT/US02/14054
§ 371 (c)(1),
(2), (4) Date: Oct. 14, 2003

(87) PCT Pub. No.: WO02/091993
PCT Pub. Date: Nov. 21, 2002

(65) Prior Publication Data
US 2004/0162304 A1 Aug. 19, 2004

Related U.S. Application Data
(60) Provisional application No. 60/290,169, filed on May 10, 2001.

(51) Int. Cl.[7] .................. C07C 39/12; C07D 221/18; C07D 211/06; A61K 31/44; A61K 31/05
(52) U.S. Cl. .................. 568/719; 568/721; 546/38; 546/195; 514/279; 514/732; 514/738
(58) Field of Search ................. 568/719, 721; 546/38, 195; 514/279, 732, 738

(56) References Cited

PUBLICATIONS

Eck, et al., "Access to the spiro hydrindandione ring system of Fredericamycin A through spiroalkylation and oxidation", Tet. Lett. 1985, vol. 26, No. 39, pp. 4725–4726.
Rama Rao, et al., "Synthesis of spiro[4,4]nonane system present in fredericamycin A+", Ind. Jour. Chem. Aug. 1991, vol. 30B, pp. 723–727.
Rama Rao, et al., "Palladium (II)–mediated Synthesis of spiro[4,4]nonane System Present in Fredericamycin A", Ind. Journ. Chem. Dec. 1988, vol. 27B, pp. 1065–1066.
Kessar, et al., "y–Alkoxylactones as Autounmasking Synthons for a One–step Construciton of 1,3–Oxygenated Cyclopentanes . . . ", J. Chem. Soc., Chem. Commun 1994, pp. 1327–1328.

*Primary Examiner*—Samuel Barts
*Assistant Examiner*—Sikarl A. Witherspoon
(74) *Attorney, Agent, or Firm*—Nicole M. Beeler; Mark R. Daniel

(57) ABSTRACT

The present invention relates to compounds and derivatives thereof, their synthesis, and their use as estrogen receptor modulators. The compounds of the instant invention are ligands for estrogen receptors and as such may be useful for treatment or prevention of a variety of conditions related to estrogen functioning including: bone loss, bone fractures, osteoporosis, cartilage degeneration, endometriosis, uterine fibroid disease, hot flashes, increased levels of LDL cholesterol, cardiovascular disease, impairment of cognitive functioning, cerebral degenerative disorders, restenosis, gynecomastia, vascular smooth muscle cell proliferation, obesity, incontinence, and cancer, in particular of the breast, uterus and prostate.

27 Claims, No Drawings

ESTROGEN RECEPTOR MODULATORS

This application claims the benefit of Provisional application No. 60/290,169, filed May 10, 2001.

BACKGROUND OF THE INVENTION

Naturally occurring and synthetic estrogens have broad therapeutic utility, including: relief of menopausal symptoms, treatment of acne, treatment of dysmenorrhea and dysfunctional uterine bleeding, treatment of osteoporosis, treatment of hirsutism, treatment of prostatic cancer, treatment of hot flashes and prevention of cardiovascular disease. Because estrogen is very therapeutically valuable, there has been great interest in discovering compounds that mimic estrogen-like behavior in estrogen responsive tissues.

For example, estrogen-like compounds would be beneficial in the treatment and prevention of bone loss. Bone loss occurs in a wide range of subjects, including women that are post-menopausal or have had a hysterectomy, patients who were or are currently being treated with corticosteroids, and patient's having gonadal dysgenesis. The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid-induced osteoporosis. All of these conditions are characterized by bone loss, resulting from an imbalance between bone resorption, i.e. breakdown, and bone formation, which continues throughout life at the rate of about 14% per year on the average. However, the rate of bone turnover differs from site to site, for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

In the U.S., there are currently about 20 million people with detectable fractures of the vertebrae due to osteoporosis. In addition, there are about 250,000 hip fractures per year attributed to osteoporosis. This clinical situation is associated with a 12% mortality rate within the first two years, while 30% of the patients require nursing home care after the fracture.

Osteoporosis affects approximately 20 to 25 million postmenopausal women in the U.S. alone. It has been theorized that the rapid loss of bone mass in these women is due to the cessation of estrogen production of the ovaries. Since studies have shown that estrogen slows the reduction of bone mass due to osteoporosis, estrogen replacement therapy is a recognized treatment for post-menopausal osteoporosis.

In addition to bone mass, estrogen appears to have an effect on the biosynthesis of cholesterol and cardiovascular health. Statistically, the rate of occurrence of cardiovascular disease is roughly equal in postmenopausal women and men; however, premenopausal women have a much lower incidence of cardiovascular disease than men. Because postmenopausal women are estrogen deficient, it is believed that estrogen plays a beneficial role in preventing cardiovascular disease. The mechanism is not well understood, but evidence indicates that estrogen can upregulate the low density lipid (LDL) cholesterol receptors in the liver to remove excess cholesterol.

Postmenopausal women given estrogen replacement therapy experience a return of lipid levels to concentrations comparable to levels associated with the premenopausal state. Thus, estrogen replacement therapy could be an effective treatment for such disease. However, the side effects associated with long term estrogen use limit the use of this alternative.

Other disease states that affect postmenopausal women include estrogen-dependent breast cancer and uterine cancer. Anti-estrogen compounds, such as tamoxifen, have commonly been used as chemotherapy to treat breast cancer patients. Tamoxifen, a dual antagonist and agonist of estrogen receptors, is beneficial in treating estrogen-dependent breast cancer. However, treatment with tamoxifen is less than ideal because tamoxifen's agonist behavior enhances its unwanted estrogenic side effects. For example, tamoxifen and other compounds that agonize estrogen receptors tend to increase cancer cell production in the uterus. A better therapy for such cancers would be an anti-estrogen compound that has negligible or nonexistent agonist properties.

Although estrogen can be beneficial for treating pathologies such as bone loss, increased lipid levels, and cancer, long-term estrogen therapy has been implicated in a variety of disorders, including an increase in the risk of uterine and endometrial cancers. These and other side effects of estrogen replacement therapy are not acceptable to many women, thus limiting its use.

Alternative regimens, such as a combined progestogen and estrogen dose, have been suggested in an attempt to lessen the risk of cancer. However, such regimens cause the patient to experience withdrawal bleeding, which is unacceptable to many older women. Furthermore, combining estrogen with progestogen reduces the beneficial cholesterol-lowering effect of estrogen therapy. In addition, the long term effects of progestogen treatment are unknown.

In addition to post-menopausal women, men suffering from prostatic cancer can also benefit from anti-estrogen compounds. Prostatic cancer is often endocrine-sensitive; androgen stimulation fosters tumor growth, while androgen suppression retards tumor growth. The administration of estrogen is helpful in the treatment and control of prostatic cancer because estrogen administration lowers the level of gonadotropin and, consequently, androgen levels.

The estrogen receptor has been found to have two forms: $ER\alpha$ and $ER\beta$. Ligands bind differently to these two forms, and each form has a different tissue specificity to binding ligands. Thus, it is possible to have compounds that are selective for $ER\alpha$ or $ER\beta$, and therefore confer a degree of tissue specificity to a particular ligand.

What is needed in the art are compounds that can produce the same positive responses as estrogen replacement therapy without the negative side effects. Also need are estrogen-like compounds that exert selective effects on different tissues of the body. Specifically, what is needed are compounds that exhibit a potent, selective affinity for $ER\alpha$, and act as antagonists on breast and uterine tissues and as agonists on bone and lipids.

The compounds of the instant invention are ligands for estrogen receptors and as such may be useful for treatment or prevention of a variety of conditions related to estrogen functioning including: bone loss, bone fractures, osteoporosis, glucocorticoid induced osteoporosis, Paget's disease, abnormally increased bone turnover, periodontal disease, tooth loss, rheumatoid arthritis, osteoarthritis, periprosthetic osteolysis, osteogenesis imperfecta, metastatic bone disease, hypercalcemia of malignancy, and multiple myeloma, cartilage degeneration, endometriosis, uterine fibroid disease, cancer of the breast, uterus or prostate, hot flashes, cardiovascular disease, impairment of cognitive function, cerebral degenerative disorders, restenosis, gynecomastia, vascular smooth muscle cell proliferation, obesity and incontinence.

SUMMARY OF THE INVENTION

The present invention relates to compounds that are capable of treating and/or preventing a variety of conditions related to estrogen functioning. One embodiment of the present invention is illustrated by a compound of Formula I, and the pharmaceutically acceptable salts and stereoisomers thereof:

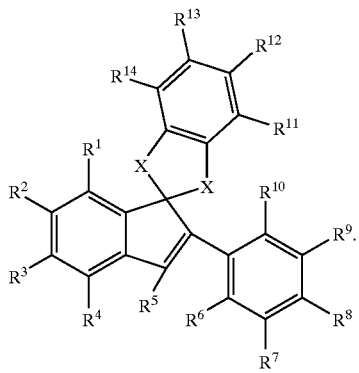

I

DETAILED DESCRIPTION OF THE INVENTION

The present invention relates to compounds useful as estrogen receptor modulators. Compounds of the present invention are described by the following chemical formula:

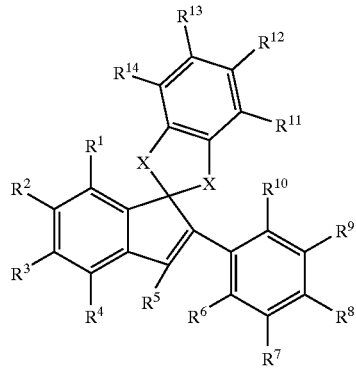

wherein each X is independently selected from the group consisting of $CH_2$, C=O, $C=CH_2$, $C=NOR^a$, $CHCH_3$, CHF, CHOH, $C(CH_3)OH$, $CF_2$ and S;
$R^1$, $R^2$, $R^3$, $R^4$, $R^6$, $R^7$, $R^8$, $R^9$ and $R^{10}$ are each independently selected from the the group consisting of $R^a$, $OR^a$, $OCO_2R^a$, $NR^aR^a$, $CO_2R^a$, CN, Cl, F and Br;
$R^{11}$, $R^{12}$, $R^{13}$ and $R^{14}$ are each independently selected from the group consisting of H, $R^b$, $OR^b$, $OCO_2R^b$, $NR^aR^b$, $CO_2R^b$, F, Cl, CN, Br;
$R^5$ is selected from the group consisting of H, F and $C_{1-6}$alkyl;
$R^a$ is selected from the group consisting of H, $C_{1-6}$alkyl and $C_{1-6}$acyl;
$R^b$ is selected from the group consisting of $C_{2-7}$alkyl and $C_{2-7}$acyl, wherein said alkyl and acyl groups may be optionally substituted with an $R^c$ group;

$R^c$ is selected from the group consisting of $OR^d$ and $NR^dR^e$,
$R^d$ and $R^e$ are each independently selected from the group consisting of H and $C_{1-7}$ alkyl;
or $R^d$ and $R^e$ can be taken together with the nitrogen atom to which they are attached to form a 4–8 membered ring, wherein said ring is optionally interrupted by one of O, NH, $NCH_3$ and S and is optionally substituted with one, two, three or four $C_{1-2}$ alkyl groups, or one or two $R^f$ groups;
$R^f$ is selected from the group consisting of $CH_2OH$ and $CH_2CH_2OH$;
or a pharmaceutically acceptable salt or stereoisomer thereof.

In one class of the invention, each X is independently selected from the group consisting of $CH_2$ and C=O. In a subclass of the invention, each X is $CH_2$. In another subclass of the invention, each X is C=O. In another subclass of the invention, one X is $CH_2$ and the other is C=O.

In another class of the invention, $R^1$, $R^2$, $R^3$, $R^4$, $R^6$, $R^7$, $R^8$, $R^9$ and $R^{10}$ are each independently selected from the group consisting of $R^a$, $OR^a$, Cl, F and Br.

In another class of the invention, $R^5$ is selected from the group consisting of H and $CH_3$;

In another class of the invention, $R^{11}$, $R^{12}$, $R^{13}$ and $R^{14}$ are each independently selected from the group consisting of H, $R^b$ and $OR^b$.

In a sublclass of the invention, $R^1$, $R^6$, $R^9$, $R^{10}$, $R^{11}$, and $R^{12}$ are H. In another subclass of the invention, $R^2$, $R^3$, $R^4$, $R^7$, and $R^8$ are each independently selected from the group consisting of H, F, and OH with the proviso that at least one of $R^2$, $R^3$, $R^4$, $R^7$, and $R^8$ is OH.

In a class of the invention, $R^b$ is $C_{2-7}$ alkyl wherein said alkyl group may be optionally substituted with an $R^c$ group.

In a class of the invention, $R^c$ is $NR^dR^e$.

In another class of the invention, $R^c$ is selected from the group consisting of $OR^d$ and $NR^dR^e$; and $R^d$ and $R^e$ can be taken together with the nitrogen atom to which they are attached to form a 6 membered ring, wherein said ring is optionally interrupted by one of O, NH, $NCH_3$ and S and is optionally substituted with one, two, three or four $C_{1-2}$ alkyl groups, and one or two $R^f$ groups.

Non-limiting examples of compounds of the present invention include:

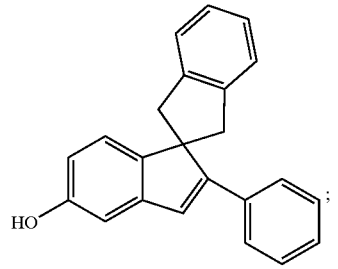

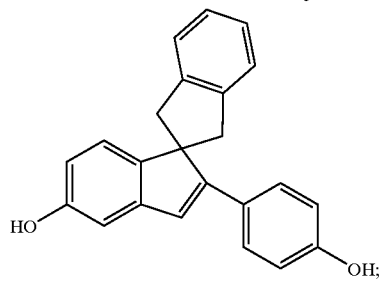

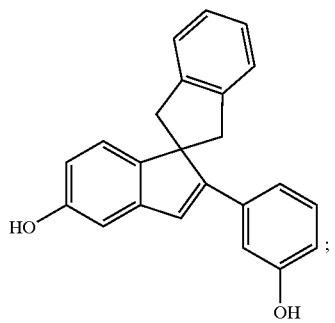

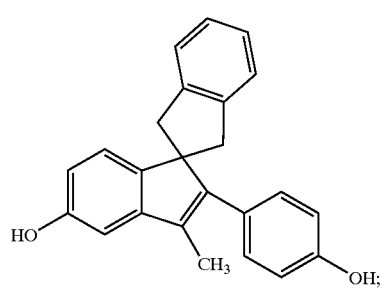

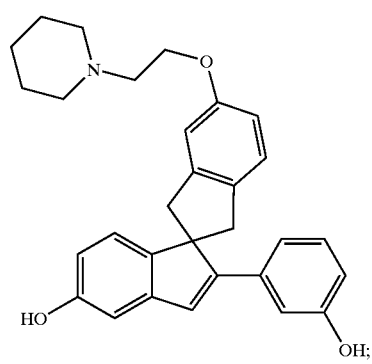

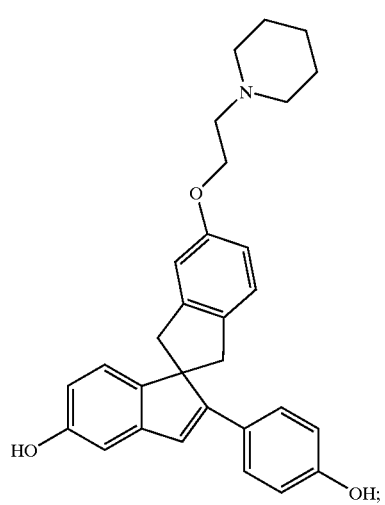

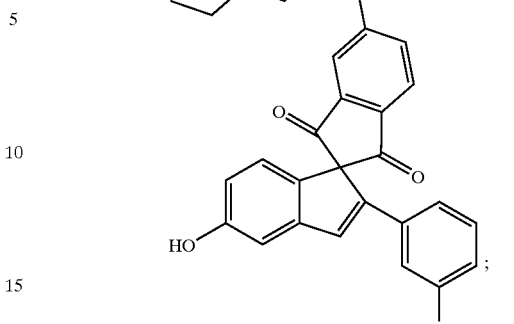

or a pharmaceutically acceptable salt or stereoisomer thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. The present invention also relates to methods for making the pharmaceutical compositions of the present invention. The present invention is also related to processes and intermediates useful for making the compounds and pharmaceutical compositions of the present invention. These and other aspects of the invention will be apparent from the teachings contained herein.

Utilities

The compounds of the present invention are selective modulators of estrogen receptors and are therefore useful to treat or prevent a variety of diseases and conditions related to estrogen receptor functioning in mammals, preferably humans.

"A variety of diseases and conditions related to estrogen receptor functioning" includes, but is not limited to, bone loss, bone fractures, osteoporosis, glucocorticoid induced osteoporosis, Paget's disease, abnormally increased bone turnover, periodontal disease, tooth loss, rheumatoid arthritis, osteoarthritis, periprosthetic osteolysis, osteogenesis imperfecta, metastatic bone disease, hypercalcemia of malignancy, and multiple myeloma, cartilage degeneration, endometriosis, uterine fibroid disease, cancer of the breast, uterus or prostate, hot flashes, cardiovascular disease, impairment of cognitive function, cerebral degenerative disorders, restenosis, gynecomastia, vascular smooth muscle cell proliferation, obesity and incontinence. In treating such conditions with the instantly claimed compounds, the required therapeutic amount will vary according to the specific disease and is readily ascertainable by those skilled in the art. Although both treatment and prevention are contemplated by the scope of the invention, the treatment of these conditions is the preferred use.

The present invention also relates to methods for eliciting an estrogen receptor modulating effect in a mammal in need thereof by administering the compounds and pharmaceutical compositions of the present invention.

The present invention also relates to methods for eliciting an estrogen receptor antagonizing effect in a mammal in need thereof by administering the compounds and pharmaceutical compositions of the present invention. The estrogen receptor antagonizing effect can be either an ERα antagonizing effect, and ERβ antagonizing effect or a mixed ERα and ERβ antagonizing effect.

The present invention also relates to methods for eliciting an estrogen receptor agonizing effect in a mammal in need thereof by administering the compounds and pharmaceutical compositions of the present invention. The estrogen receptor agonizing effect can be either an ERα agonizing effect, and ERβ agonizing effect or a mixed ERα and ERβ agonizing effect.

The present invention also relates to methods for treating or preventing disorders related to estrogen functioning, bone loss, bone fractures, osteoporosis, glucocorticoid induced osteoporosis, Paget's disease, abnormally increased bone turnover, periodontal disease, tooth loss, rheumatoid arthritis, osteoarthritis, periprosthetic osteolysis, osteogenesis imperfecta, metastatic bone disease, hypercalcemia of malignancy, and multiple myeloma, cartilage degeneration, endometriosis, uterine fibroid disease, cancer of the breast, uterus or prostate, hot flashes, cardiovascular disease, impairment of cognitive function, cerebral degenerative disorders, restenosis, gynecomastia, vascular smooth muscle cell proliferation, obesity and incontinence in a mammal in need thereof by administering the compounds and pharmaceutical compositions of the present invention. Exemplifying the invention is a method of treating or preventing osteoporosis. Exemplifying the invention is a method of treating or preventing bone loss. Exemplifying the invention is a method of treating or preventing metastatic bone disease. Exemplifying the invention is a method of treating or preventing cancer. Exemplifying the invention is a method of treating or preventing cardiovascular disease.

An embodiment of the invention is a method for treating or preventing cancer, especially of the breast, uterus or prostate, in a mammal in need thereof by administering the compounds and pharmaceutical compositions of the present invention. The utility of SERMs for the treatment of breast, uterine or prostate cancer is known in the literature, see T. J. Powles, "Breast cancer prevention," Oncologist 2002; 7(1) :60–4; Park, W. C. and Jordan, V. C., "Selective estrogen receptor modulators (SERMS) and their roles in breast cancer prevention." Trends Mol Med. 2002 February;8(2) :82–8; Wolff, A. C. et al., "Use of SERMs for the adjuvant therapy of early-stage breast cancer," Ann N Y Acad. Sci. 2001 December;949:80–8; Steiner, M. S. et al., "Selective estrogen receptor modulators for the chemoprevention of prostate cancer," Urology 2001 April; 57(4 Suppl 1):68–72.

Another embodiment of the invention is a method of treating or preventing metastatic bone disease in a mammal in need thereof by administering to the mammal a therapeutically effective amount of any of the compounds or pharmaceutical compositions described above. The utility of SERMS in the treatment of metastatic bone disease is known in the literature, see, Campisi, C. et al., "Complete resoultion of breast cancer bone metastasis through the use of beta-interferon and tamoxifen," Eur J Gynaecol Oncol 1993;14 (6):479–83.

Another embodiment of the invention is a method of treating or preventing gynecomastia in a mammal in need thereof by administering to the mammal a therapeutically effective amount of any of the compounds or pharmaceutical compositions described above. The utility of SERMS in the treatment of gynecomastia is known in the literature, see, Ribeiro, G. and Swindell R., "Adjuvant tamoxifen for male breast cancer." Br J Cancer 1992;65:252–254; Donegan, W., "Cancer of the Male Breast," JGSM Vol. 3, Issue 4, 2000.

Another embodiment of the invention is a method of treating or preventing post-menopausal osteoporosis, glucocorticoid osteoporosis, hypercalcemia of malignancy, bone loss and bone fractures in a mammal in need thereof by administering to the mammal a therapeutically effective amount of any of the compounds or pharmaceutical compositions described above. The utility of SERMs to treat or prevent osteoporosis, hypercalcemia of malignancy, bone loss or bone fractures is known in the literature, see Jordan, V. C. et al., "Selective estrogen receptor modulation and reduction in risk of breast cancer, osteoporosis and coronary heart disease," Natl Cancer Inst 2001 October; 93(19): 1449–57; Bjarnason, N H et al., "Six and twelve month changes in bone turnover are realted to reduction in vertebral fracture risk during 3 years of raloxifene treatment in postemenopausal osteoporosis," Osteoporosis Int 2001; 12(11):922–3; Fentiman I. S., "Tamoxifen protects against steroid-induced bone loss," Eur J Cancer 28:684–685 (1992); Rodan, G. A. et al., "Therapeutic Approaches to Bone Diseases," Science Vol 289, 1 Sep. 2000.

Another embodiment of the invention is a method of treating of preventing periodontal disease or tooth loss in a mammal in need thereof by administering to the mammal a therapeutically effective amount of any of the compounds or pharmaceutical compositions described above. The use of SERMs to treat periodontal disease or tooth loss in a mammal is known in the literature, see Rodan, G. A. et al., "Therapeutic Approaches to Bone Diseases," Science Vol 289, 1 Sep. 2000 pp. 1508–14.

Another embodiment of the invention is a method of treating of preventing Paget's disease in a mammal in need thereof by administering to the mammal a therapeutically effective amount of any of the compounds or pharmaceutical compositions described above. The use of SERMs to treat Paget's disease in a mammal is known in the literature, see Rodan, G. A. et al., "Therapeutic Approaches to Bone Diseases," Science Vol 289, 1 Sep. 2000 pp. 1508–14.

Another embodiment of the invention is a method of treating or preventing uterine fibroid disease in a mammal in need thereof by administering to the mammal a therapeutically effective amount of any of the compounds or pharmaceutical compositions described above. The use of SERMS to treat uterine fibroids, or uterine leiomyomas, is known in the literature, see Palomba, S., et al, "Effects of raloxifene treatment on uterine leiomyomas in postmenopausal women," Fertil Steril. 2001 July;76(1):38–43.

Another embodiment of the invention is a method of treating or preventing obesity in a mammal in need thereof by administering to the mammal a therapeutically effective amount of any of the compounds or pharmaceutical compositions described above. The use of SERMs to treat obesity is known in the literature, see Picard, F. et al., "Effects of the estrogen antagonist EM-652.HCl on energy balance and lipid metabolism in ovariectomized rats," Int J Obes Relat Metab Disord. 2000 July;24(7):830–40.

Another embodiment of the invention is a method of treating or preventing cartilage degeneration, rheumatoid arthritis or osteoarthritis in a mammal in need thereof by administering to the mammal a therapeutically effective amount of any of the compounds or pharmaceutical compositions described above. The use of SERMs to treat cartilage degeneration, rheumatoid arthritis or osteoarthritis is known in the literature, see Badger, A. M. et al., "Idoxifene, a novel selective estrogen receptor modulator, is effective in a rat model of adjuvant-induced arthritis." J Pharmacol Exp Ther. 1999 December;291(3):1380–6.

Another embodiment of the invention is a method of treating or preventing endometriosis in a mammal in need thereof by administering to the mammal a therapeutically effective amount of any of the compounds or pharmaceutical compositions described above. The use of SERMs to treat endometriosis is known in the art, see Steven R. Goldstein, "The Effect of SERMs on the Endometrium," Annals of the New York Academy of Sciences 949:237–242 (2001).

Another embodiment of the invention is a method of treating or preventing urinary incontinence in a mammal in need thereof by administering to the mammal a therapeutically effective amount of any of the compounds or pharmaceutical compositions described above. The use of SERMs to treat urinary incontinence is known in the art, see, Goldstein, S. R., "Raloxifene effect on frequency of surgery for pelvic floor relaxation," Obstet Gynecol. 2001 July;98 (1):91–6.

Another embodiment of the invention is a method of treating or preventing cardiovascular disease, restenosis, lowering levels of LDL cholesterol and inhibiting vascular smooth muscle cell proliferation in a mammal in need thereof by administering to the mammal a therapeutically effective amount of any of the compounds or pharmaceutical compositions described above. The utility of SERMs in treating or preventing cardiovascular disease, restenosis, lowering levels of LDL cholesterol and inhibiting vascular smooth muscle cell proliferation is known in the art, see Nuttall, M E et al., "Idoxifene: a novel selective estrogen receptor modulator prevents bone loss and lowers cholesterol levels in ovariectomized rats and decreases uterine weight in intact rats," Endocrinology 1998 December; 139 (12):5224–34; Jordan, V. C. et al., "Selective estrogen receptor modulation and reduction in risk of breast cancer, osteoporosis and coronary heart disease," Natl Cancer Inst 2001 October; 93(19):1449–57; Guzzo J A., "Selective estrogen receptor modulators—a new age of estrogens in cardiovascular disease?," Clin Cardiol 2000 January;23(1):15–7; Simoncini T, Genazzani A R., "Direct vascular effects of estrogens and selective estrogen receptor modulators," Curr Opin Obstet Gynecol 2000 June;12(3):181–7.

Another embodiment of the invention is a method of treating or preventing the impairment of cognitive functioning or cerebral degenerative disorders in a mammal in need thereof by administering to the mammal a therapeutically effective amount of any of the compounds or pharmaceutical compositions described above. The utility of SERMs to prevent the impairment of cognitive functioning is known in the art, see Yaffe, K., K. Krueger, S. Sarkar, et al. 2001. Cognitive function in postmenopausal women treated with raloxifene. N. Eng. J. Med. 344: 1207–1213.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, metastatic bone disease and/or disorders related to estrogen functioning.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

In the case of tablets for oral use, carriers which are commonly used include lactose and corn starch, and lubricating agents, such as magnesium stearate, are commonly added. For oral administration in capsule form, useful diluents include lactose and dried corn starch. For oral use of a therapeutic compound according to this invention, the selected compound may be administered, for example, in the form of tablets or capsules, or as an aqueous solution or suspension. For oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The instant compounds are also useful in combination with known agents useful for treating or preventing bone loss, bone fractures, osteoporosis, glucocorticoid induced osteoporosis, Paget's disease, abnormally increased bone turnover, periodontal disease, tooth loss, rheumatoid arthritis, osteoarthritis, periprosthetic osteolysis, osteogenesis imperfecta, metastatic bone disease, hypercalcemia of malignancy, and multiple myeloma, cartilage degeneration, endometriosis, uterine fibroid disease, cancer of the breast, uterus or prostate, hot flashes, cardiovascular disease, impairment of cognitive function, cerebral degenerative disorders, restenosis, gynecomastia, vascular smooth muscle cell proliferation, obesity and incontinence. Combinations of the presently disclosed compounds with other agents useful in treating or preventing osteoporosis or other bone disorders are within the scope of the invention. A person of ordinary skill in the art would be able to discern which combinations of agents would be useful based on the particular characteristics of the drugs and the disease involved. Such agents include the following: an organic bisphosphonate; a cathepsin K inhibitor; an estrogen or an estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; calcitonin; Vitamin D or a synthetic Vitamin D analogue; selective serotonin reuptake inhibitors (SSRIs); and the pharmaceutically acceptable salts and mixtures thereof. A preferred combination is a compound of the present invention and an organic bisphosphonate. Another preferred combination is a compound of the present invention and a cathepsin K inhibitor. Another preferred combination is a compound of the present invention and an estrogen. Another preferred combination is a compound of the present invention and an androgen receptor modulator. Another preferred combination is a compound of the present invention and an osteoblast anabolic agent.

"Organic bisphosphonate" includes, but is not limited to, compounds of the chemical formula

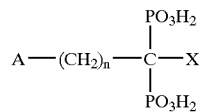

wherein n is an integer from 0 to 7 and wherein A and X are independently selected from the group consisting of H, OH, halogen, $NH_2$, SH, phenyl, C1–C30 alkyl, C3–C30 branched or cycloalkyl, bicyclic ring structure containing two or three N, C1–C30 substituted alkyl, C1–C10 alkyl substituted $NH_2$, C3–C10 branched or cycloalkyl substituted $NH_2$, C1–C10 dialkyl substituted $NH_2$, C1–C10 alkoxy, C1–C10 alkyl substituted thio, thiophenyl, halophenylthio, C1–C10 alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a C3–C10 ring.

In the foregoing chemical formula, the alkyl groups can be straight, branched, or cyclic, provided sufficient atoms are selected for the chemical formula. The C1–C30 substituted alkyl can include a wide variety of substituents, nonlimiting examples which include those selected from the group consisting of phenyl, pyridyl, furanyl, pyrrolidinyl, imidazonyl, $NH_2$, C1–C10 alkyl or dialkyl substituted $NH_2$, OH, SH, and C1–C10 alkoxy.

The foregoing chemical formula is also intended to encompass complex carbocyclic, aromatic and hetero atom structures for the A and/or X substituents, nonlimiting examples of which include naphthyl, quinolyl, isoquinolyl, adamantyl, and chlorophenylthio.

Pharmaceutically acceptable salts and derivatives of the bisphosphonates are also useful herein. Non-limiting examples of salts include those selected from the group consisting alkali metal, alkaline metal, ammonium, and mono-, di-, tri-, or tetra-C1–C30-alkyl-substituted ammonium. Preferred salts are those selected from the group consisting of sodium, potassium, calcium, magnesium, and ammonium salts. More preferred are sodium salts. Non-limiting examples of derivatives include those selected from the group consisting of esters, hydrates, and amides.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated. Because of the mixed nomenclature currently in use by those of ordinary skill in the art, reference to a specific weight or percentage of a bisphosphonate compound in the present invention is on an acid active weight basis, unless indicated otherwise herein. For example, the phrase "about 5 mg of a bone resorption inhibiting bisphosphonate selected from the group consisting of alendronate, pharmaceutically acceptable salts thereof, and mixtures thereof, on an alendronic acid active weight basis" means that the amount of the bisphosphonate compound selected is calculated based on 5 mg of alendronic acid.

Non-limiting examples of bisphosphonates useful herein include the following:

Alendronic acid, 4-amino-1-hydroxybutylidene-1,1-bisphosphonic acid.

Alendronate (also known as alendronate sodium or alendronate monosodium trihydrate), 4-amino-1-hydroxybutylidene-1,1-bisphosphonic acid monosodium trihydrate.

Alendronic acid and alendronate are described in U.S. Pat. No. 4,922,007, to Kieczykowski et al., issued May 1, 1990; U.S. Pat. No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997, all of which are incorporated by reference herein in their entirety.

Cycloheptylaminomethylene-1,1-bisphosphonic acid, YM 175, Yamanouchi (incadronate, formerly known as cimadronate), as described in U.S. Pat. No. 4,970,335, to Isomura et al., issued Nov. 13, 1990, which is incorporated by reference herein in its entirety.

1,1-dichloromethylene-1,1-diphosphonic acid (clodronic acid), and the disodium salt (clodronate, Procter and Gamble), are described in Belgium Patent 672,205 (1966) and *J. Org. Chem* 32, 4111 (1967), both of which are incorporated by reference herein in their entirety.

1-hydroxy-3-(1-pyrrolidinyl)-propylidene-1,1-bisphosphonic acid (EB-1053).

1-hydroxyethane-1,1-diphosphonic acid (etidronic acid).

1-hydroxy-3-(N-methyl-N-pentylamino)propylidene-1,1-bisphosphonic acid, also known as BM-210955, Boehringer-Mannheim (ibandronate), is described in U.S. Pat. No. 4,927,814, issued May 22, 1990, which is incorporated by reference herein in its entirety.

1-hydroxy-2-imidazo-(1,2-a)pyridin-3-yethylidene (minodronate).

6-amino-1-hydroxyhexylidene-1,1-bisphosphonic acid (neridronate).

3-(dimethylamino)-1-hydroxypropylidene-1,1-bisphosphonic acid (olpadronate).

3-amino-1-hydroxypropylidene-1,1-bisphosphonic acid (pamidronate).

[2-(2-pyridinyl)ethylidene]-1,1-bisphosphonic acid (piridronate) is described in U.S. Pat. No. 4,761,406, which is incorporated by reference in its entirety.

1-hydroxy-2-(3-pyridinyl)-ethylidene-1,1-bisphosphonic acid (risedronate).

(4-chlorophenyl)thiomethane-1,1-disphosphonic acid (tiludronate) as described in U.S. Pat. No. 4,876,248, to Breliere et al., Oct. 24, 1989, which is incorporated by reference herein in its entirety.

1-hydroxy-2-(1H-imidazol-1-yl)ethylidene-1,1-bisphosphonic acid (zoledronate).

Nonlimiting examples of bisphosphonates include alendronate, cimadronate, clodronate, etidronate, ibandronate, incadronate, minodronate, neridronate, olpadronate, pamidronate, piridronate, risedronate, tiludronate, and zolendronate, and pharmaceutically acceptable salts and esters thereof. A particularly preferred bisphosphonate is alendronate, especially a sodium, potassium, calcium, magnesium or ammonium salt of alendronic acid. Exemplifying the preferred bisphosphonate is a sodium salt of alendronic acid, especially a hydrated sodium salt of alendronic acid. The salt can be hydrated with a whole number of moles of water or non whole numbers of moles of water. Further exemplifying the preferred bisphosphonate is a hydrated sodium salt of alendronic acid, especially when the hydrated salt is alendronate monosodium trihydrate.

It is recognized that mixtures of two or more of the bisphosphonate actives can be utilized.

The precise dosage of the organic bisphosphonate will vary with the dosing schedule, the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. Generally, an appropriate amount of bisphosphonate is chosen to obtain a bone resorption inhibiting effect, i.e. a bone resorption inhibiting amount of the bisphosphonate is administered. For humans, an effective oral dose of bisphosphonate is typically from about 1.5 to about 6000 µg/kg body weight and preferably about 10 to about 2000 µg/kg of body weight. For alendronate monosodium trihydrate, common human doses which are administered are generally in the range of about 2 mg/day to about 40 mg/day, preferably about 5 mg/day to about 40 mg/day. In the U.S. presently approved dosages for alendronate monosodium trihydrate are 5 mg/day for preventing osteoporosis, 10 mg/day for treating osteoporosis, and 40 mg/day for treating Paget's disease.

In alternative dosing regimens, the bisphosphonate can be administered at intervals other than daily, for example once-weekly dosing, twice-weekly dosing, biweekly dosing, and twice-monthly dosing. In a once weekly dosing regimen, alendronate monosodium trihydrate would be administered at dosages of 35 mg/week or 70 mg/week. The bisphosphonates may also be administered monthly, ever six months, yearly or even less frequently, see WO 01/97788 (published Dec. 27, 2001) and WO 01/89494 (published Nov. 29, 2001).

"Estrogen" includes, but is not limited to naturally occurring estrogens [7-estradiol ($E_2$), estrone ($E_1$), and estriol ($E_3$)], synthetic conjugated estrogens, oral contraceptives and sulfated estrogens. See, Gruber C J, Tschugguel W, Schneeberger C, Huber J C., "Production and actions of estrogens" N Engl J Med 2002 Jan. 31;346(5):340–52.

"Estrogen receptor modulators" refers to compounds which interfere or inhibit the binding of estrogen to the receptor, regardless of mechanism. Examples of estrogen receptor modulators include, but are not limited to, estrogen, progestogen, estradiol, droloxifene, raloxifene, lasofoxifene, TSE-424, tamoxifen, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenylhydrazone, and SH646.

"Cathepsin K inhibitors" refers to compounds which interfere with the activity of the cysteine protease cathepsin K. Nonlimiting examples of cathepsin K inhibitors can be found in PCT publications WO 00/55126 to Axys Pharmaceuticals and WO 01/49288 to Merck Frosst Canada & Co. and Axys Pharmaceuticals.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"An inhibitor of osteoclast proton ATPase" refers to an inhibitor of the proton ATPase, which is found on the apical membrane of the osteoclast, and has been reported to play a significant role in the bone resorption process. This proton pump represents an attractive target for the design of inhibitors of bone resorption which are potentially useful for the treatment and prevention of osteoporosis and related metabolic diseases. See C. Farina et al., "Selective inhibitors of the osteoclast vacuolar proton ATPase as novel bone antiresorptive agents," DDT, 4: 163–172 (1999)), which is hereby incorporated by reference in its entirety.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820, 850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342, 952) and cerivastatin (also known as rivastatin and BAY-CHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85–89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

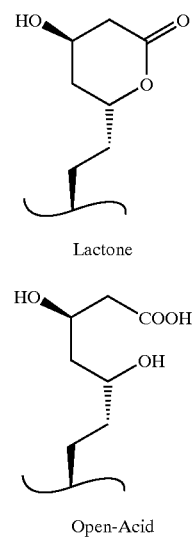

Lactone

Open-Acid

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

As used above, "integrin receptor antagonists" refers to compounds which selectively antagonize, inhibit or counteract binding of a physiological ligand to the $\alpha_v\beta_3$ integrin, to compounds which selectively antagonize, inhibit or counter-act binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. H. N. Lode and coworkers in PNAS USA 96: 1591–1596 (1999) have observed synergistic effects between an antiangiogenic αv integrin antagonist and a tumor-specific antibody-cytokine (interleukin-2) fusion protein in the eradication of spontaneous tumor metastases. Their results suggested this combination as having potential for the treatment of cancer and metastatic tumor growth. $\alpha_v\beta_3$ integrin receptor antagonists inhibit bone resorption through a new mechanism distinct from that of all currently available drugs. Integrins are heterodimeric transmembrane adhesion receptors that mediate cell-cell and cell-matrix interactions. The α and β integrin subunits interact non-covalently and bind extracellular matrix ligands in a divalent cation-dependent manner. The most abundant integrin on osteoclasts is $\alpha_v\beta_3$ (>$10^7$/ osteoclast), which appears to play a rate-limiting role in cytoskeletal organization important for cell migration and polarization. The $\alpha_v\beta_3$ antagonizing effect is selected from inhibition of bone resorption, inhibition of restenosis, inhibition of macular degeneration, inhibition of arthritis, and inhibition of cancer and metastatic growth.

"An osteoblast anabolic agent" refers to agents that build bone, such as PTH. The intermittent administration of parathyroid hormone (PTH) or its amino-terminal fragments and analogues have been shown to prevent, arrest, partially reverse bone loss and stimulate bone formation in animals and humans. For a discussion refer to D. W. Dempster et al., "Anabolic actions of parathyroid hormone on bone," Endocr Rev 14: 690–709 (1993). Studies have demonstrated the clinical benefits of parathyroid hormone in stimulating bone formation and thereby increasing bone mass and strength. Results were reported by R M Neer et al., in New Eng J Med 344 1434–1441 (2001).

In addition, parathyroid hormone-related protein fragments or analogues, such as PTHrP-(1–36) have demonstrated potent anticalciuric effects [see M. A. Syed et al., "Parathyroid hormone-related protein-(1–36) stimulates renal tubular calcium reabsorption in normal human volunteers: implications for the pathogenesis of humoral hypercalcemia of malignancy," JCEM 86: 1525–1531 (2001)] and may also have potential as anabolic agents for treating osteoporosis.

Calcitonin is a 32 amino acid pepetide produced primarily by the thyroid which is known to participate in calcium and phosphorus metabolism. Calcitonin suppresses resorption of bone by inhibiting the activity of osteoclasts. Thus, calcitonin can allow osteoblasts to work more effectively and build bone.

"Vitamin D" includes, but is not limited to, vitamin $D_3$ (cholecalciferol) and vitamin $D_2$ (ergocalciferol), which are naturally occurring, biologically inactive precursors of the hydroxylated biologically active metabolites of vitamin D: 1α-hydroxy vitamin D; 25-hydroxy vitamin D, and 1α,25-dihydroxy vitamin D. Vitamin $D_2$ and vitamin $D_3$ have the same biological efficacy in humans. When either vitamin $D_2$ or $D_3$ enters the circulation, it is hydroxylated by cytochrome $P_{450}$-vitamin D-25-hydroxylase to give 25-hydroxy vitamin D. The 25-hydroxy vitamin D metabolite is biologically inert and is further hydroxylated in the kidney by cytochrome P450-monooxygenase, 25 (OH) D-1α-hydroxylase to give 1,25-dihydroxy vitamin D. When serum calcium decreases, there is an increase in the production of parathyroid hormone (PTH), which regulates calcium homeostasis and increases plasma calcium levels by increasing the conversion of 25-hydroxy vitamin D to 1,25-dihydroxy vitamin D.

1,25-dihydroxy vitamin D is thought to be reponsible for the effects of vitamin D on calcium and bone metabolism. The 1,25-dihydroxy metabolite is the active hormone required to maintain calcium absorption and skeletal integrity. Calcium homeostasis is maintained by 1,25 dihydroxy vitamin D by inducing monocytic stem cells to differentiate into osteoclasts and by maintaining calcium in the normal range, which results in bone mineralization by the deposition of calcium hydroxyapatite onto the bone surface, see Holick, M F, Vitamin D photobiology, metabolism, and clinical applications, In: DeGroot L, Besser H, Burger H G, eg al., eds. *Endocrinology*, $3^{rd}$ ed., 990–1013 (1995). However, elevated levels of 1α,25-dihydroxy vitamin $D_3$ can result in an increase of calcium concentration in the blood and in the abnormal control of calcium concentration by bone metabolism, resulting in hypercalcemia. 1α,25-dihydroxy vitamin $D_3$ also indirectly regulates osteoclastic activity in bone metabolism and elevated levels may be expected to increase excessive bone resorption in osteoporosis.

"Synthetic vitamin D analogues" includes non-naturally occurring compounds that act like vitamin D.

Selective Serotonin Reuptake Inhibitors act by increasing the amount of serotonin in the brain. SSRIs have been used successfully for a decade in the United States to treat depression. Non-limiting examples of SSRIs include fluoxetine, paroxetine, sertraline, citalopram, and fluvoxamine. SSRIs are also being used to treat disoreders realted to estrogen functioning, suchs as premenstrual syndrome and premenstrual dysmorphic disorder. See Sundstrom-Poromaa I, Bixo M, Bjorn I, Nordh O., "Compliance to antidepressant drug therapy for treatment of premenstrual syndrome," J Psychosom Obstet Gynaecol 2000 December;21(4):205–11.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a bisphosphonate, etc.), "administration" and its variants are each understood to include concurrent and sequential introduction of the compound or prodrug thereof and other agents. The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

The present invention also encompasses a pharmaceutical composition useful in the treatment of osteoporosis or other bone disorders, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment. Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The compounds of the present invention can be used in combination with other agents useful for treating estrogen-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating cathepsin-mediated conditions includes in principle any combination with any pharmaceutical composition useful for treating disorders related to estrogen functioning.

The scope of the invetion therefore encompasses the use of the instantly claimed compounds in combination with a second agent selected from: an organic bisphosphonate; a cathepsin K inhibitor; an estrogen; an estrogen receptor modulator; an androgen receptor modulator; an inhibitor of osteoclast proton ATPase; an inhibitor of HMG-CoA reductase; an integrin receptor antagonist; an osteoblast anabolic agent; calcitonin; Vitamin D; a synthetic Vitamin D analogue; a selective serotonin reuptake inhibitor; and the pharmaceutically acceptable salts and mixtures thereof.

These and other aspects of the invention will be apparent from the teachings contained herein.

Definitions

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The terms "treating" or "treatment" of a disease as used herein includes: preventing the disease, i.e. causing the clinical symptoms of the disease not to develop in a mammal that may be exposed to or predisposed to the disease but does not yet experience or display symptoms of the disease; inhibiting the disease, i.e., arresting or reducing the development of the disease or its clinical symptoms; or relieving the disease, i.e., causing regression of the disease or its clinical symptoms.

The term "bone resorption," as used herein, refers to the process by which osteoclasts degrade bone.

The term "alkyl" shall mean a substituting univalent group derived by conceptual removal of one hydrogen atom from a straight or branched-chain acyclic saturated hydrocarbon (i.e., —$CH_3$, —$CH_2CH_3$, —$CH_2CH_2CH_3$, —CH($CH_3$)$_2$, —$CH_2CH_2CH_2CH_3$, —$CH_2CH(CH_3)_2$, —C($CH_3$)$_3$, etc.).

The term "acyl" shall mean a substituting univalent group derived by conceptual removal of the aldehyde hydrogen atom from a straight or branched-chain acyclic saturated aldehyde, i.e., —C(O)H, —C(O)$CH_3$, —C(O)$CH_2CH_3$, —C(O)$CH_2CH_2CH_3$, —C(O)CH($CH_3$)$_2$, —C(O)$CH_2CH_2CH_2CH_3$, —C(O)$CH_2CH(CH_3)_2$, —C(O)C($CH_3$)$_3$, etc.

The term "halo" shall include iodo, bromo, chloro and fluoro.

The term "oxy" means an oxygen (O) atom. The term "thio" means a sulfur (S) atom. The term "oxo" means =O. The term "oximino" means the =N—O group.

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. Also when compounds of Formula I contain groups such as hydroxy, carboxy, thiol or any group containing a nitrogen atom(s), these groups can be protected with a suitable protecting groups. A comprehensive list of suitable protective groups can be found in T. W. Greene, Protective Groups in Organic Synthesis, John Wiley & Sons, Inc. 1981, the disclosure of which is incorporated herein by reference in its entirety. The protected derivatives of compounds of Formula I can be prepared by methods well known in the art.

The alkyl substituents may be unsubstituted or unsubstituted, unless specifically defined otherwise. For example, a ($C_1$–$C_6$)alkyl may be substituted with one or more substituents selected from OH, oxo, halogen, alkoxy, dialkylamino, or heterocyclyl, such as morpholinyl, piperidinyl, and so on. In the case of a disubstituted alkyl, for instance, wherein the substituents are oxo and OH, the following are included in the definition: —(C=O)$CH_2$CH(OH)$CH_3$, —(C=O)OH, —$CH_2$(OH)$CH_2$CH(O), and so on.

In the compounds of the present invention, alkyl groups can be further substituted by replacing one or more hydrogen atoms be alternative non-hydrogen groups. These include, but are not limited to, halo, hydroxy, mercapto, amino, carboxy, cyano and carbamoyl.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The compounds of the present invention may have asymmetric centers, chiral axes, and chiral planes (as described in: E. L. Eliel and S. H. Wilen, *Stereo-chemistry of Carbon Compounds*, John Wiley & Sons, New York, 1994, pages 1119–1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

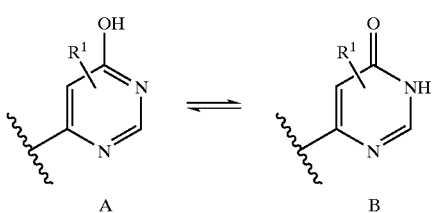

When any variable (e.g. $R^1$, $R^2$, $R^3$ etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring carbon atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

Under standard nonmenclature used throughout this disclosure, the terminal portion of the designated side chain is described first, followed by the adjacent functionality toward the point of attachment. For example, a $C_{1-5}$ alkyl-carbonylamino $C_{1-6}$ alkyl substituent is equivalent to

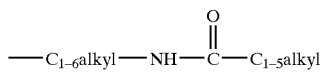

In choosing compounds of the present invention, one of ordinary skill in the art will recognize that the various substituents, i.e. $R^1, R^2, R^3, R^4, R^5, R^6, R^7, R^8, R^9, R^{10}, R^{11}, R^{12}, R^{13}, R^{14}, R^a, R^b, R^c, R^d, R^e, R^f$, and X are to be chosen in conformity with well-known principles of chemical structure connectivity.

Representative compounds of the present invention typically display submicromolar affinity for alpha and/or beta estrogen receptors. Compounds of this invention are therefore useful in treating mammals suffering from disorders related to estrogen functioning.

The compounds of the present invention are available in racemic form or as individual enantiomers. For convenience, some structures are graphically represented as a single enantiomer but, unless otherwise indicated, is meant to include both racemic and enantiomerically pure forms. Where cis and trans sterochemistry is indicated for a compound of the present invention, it should be noted that the stereochemistry should be construed as relative, unless indicated otherwise. For example, a (+) or (−) designation should be construed to represent the indicated compound with the absolute stereochemistry as shown.

Racemic mixtures can be separated into their individual enantiomers by any of a number of conventional methods. These include, but are not limited to, chiral chromatography, derivatization with a chiral auxiliary followed by separation by chromatography or crystallization, and fractional crystallization of diastereomeric salts. Deracemization procedures may also be employed, such as enantiomeric protonation of a pro-chiral intermediate anion, and the like.

The compounds of the present invention can be used in combination with other agents useful for treating estrogen-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating estrogen-mediated conditions includes in principle any combination with any pharmaceutical composition useful for treating disorders related to estrogen functioning.

The pharmaceutically acceptable salts of the compounds of this invention include the conventional non-toxic salts of the compounds of this invention as formed inorganic or organic acids. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. The preparation of the pharmaceutically acceptable salts described above and other typical pharmaceutically acceptable salts is more fully described by Berg et al., "Pharmaceutical Salts," J. Pharm. Sci., 1977:66:1–19, hereby incorporated by reference. The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The novel compounds of the present invention can be prepared according to the following general schemes, using appropriate materials, and are further exemplified by the subsequent specific examples. The compounds illustrated in the examples are not, however, to be construed as forming the only genus that is considered as the invention. Those skilled in the art will readily understand that known variations of the conditions and processes of the following preparative procedures can be used to prepare these compounds. All temperatures are degrees Celsius unless otherwise noted.

EXAMPLE 1

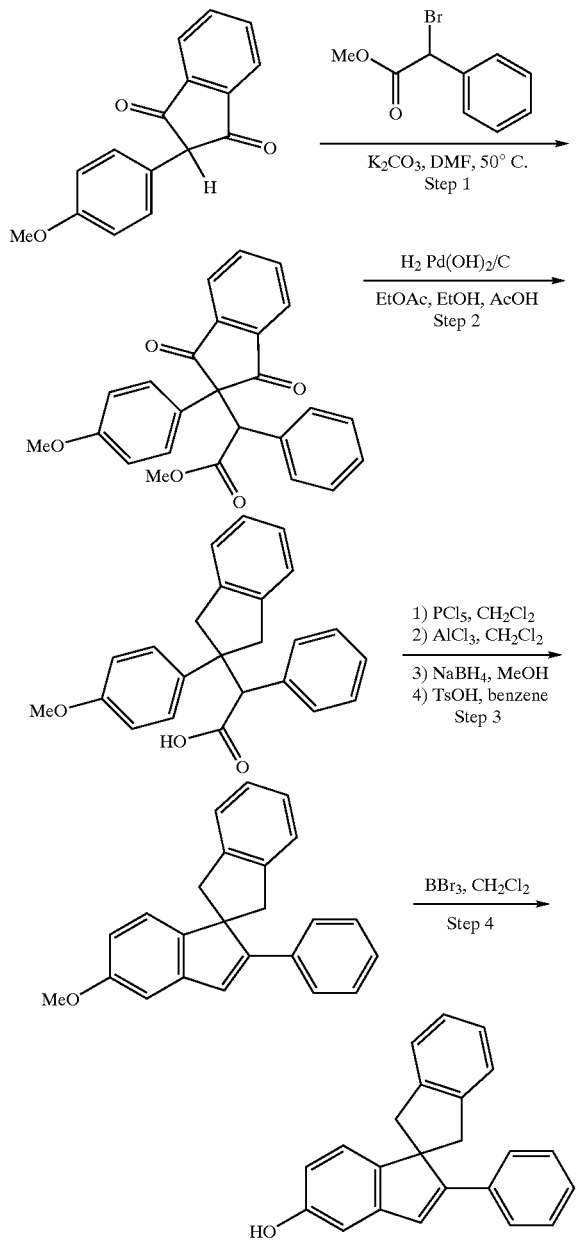

2-Phenyl-5-hydroxy-1',3'-dihydro-spiro[1H-indene-1,2'-[2H]indene]

Step 1: Potassium carbonate (0.86 g, 6.25 mmol) was added to a solution of anisindione (1.26 g, 5 mmol) in dry dimethylformamide (30 mL). The resulting dark red mixture was stirred at room temperature for 10 minutes then a solution of methyl-α-bromo-phenylacetate (1.50 g, 6.5 mmol) in dimethylformamide (10 mL) was added. The resulting mixture was stirred at 50° C. for 15 minutes (color changed from dark red to light orange) then partitioned between half-saturated aqueous ammonium chloride (250 mL) and ethyl acetate (200 mL). The aqueous layer was extracted with ethyl acetate (150 mL) and the combined organic layers were dried (MgSO$_4$), filtered, and evaporated to an orange oil. The crude product was purified by recrystallization from hexane/ethyl acetate to afford the product as a white crystalline solid (mp 158–158.5° C.).

Step 2: Glacial acetic acid (2 mL) was added to a solution of the product of step 1 (1.70 g, 4.25 mmol) in 100 mL of 1:1 ethyl acetate:ethanol then 20% palladium hydroxide on carbon (200 mg) was added. The reaction vessel was evacuated and filled twice with nitrogen gas then evacuated and filled twice with hydrogen gas and stirred under an atmosphere of hydrogen gas (balloon) for 68 hours. The reaction mixture was then diluted with ethyl acetate (50 mL) and filtered through Celite®. The Celite® was washed with ethyl acetate (2×50 mL) and the combined filtrates were evaporated to an off-white foam. This material was recrystallized from hexane/ethyl acetate to afford the product as a white crystalline solid (mp 139–140.5° C.).

Step 3: Phosphorus pentachloride (0.25 g, 1.2 mmol) was added in two equal portions to a cold (ice bath) solution of the product of step 2 (0.358 g, 1.0 mmol) in dichloromethane (10 mL). The resulting mixture was stirred at 0° C. for 1 hour then cooled to −20° C. Aluminum chloride (0.167 g, 1.25 mmol) was added and the resulting orange solution was stirred at −20° C. for 1 hour (color changed to brick red). The mixture was then diluted with ethyl acetate (50 mL) (color changed back to orange) then water (50 mL) was added (color changed to light yellow). The organic layer was washed sequentially with 5% aqueous NaHCO$_3$ (50 mL) and saturated aqueous NaCl (25 mL) then dried (MgSO$_4$), filtered, and evaporated to a yellow solid. The crude ketone thus obtained was dissolved in 12 mL of 1:1 tetrahydrofuran:methanol then cooled in an ice bath as sodium borohydride (0.189 g, 5 mmol) was added slowly in portions (CAUTION: vigorous reaction, gas evolution). The resulting mixture was stirred at room temperature for 2 hours then additional sodium borohydride (0.090 g, 2.5 mmol) was added. After an additional 30 minutes at room temperature the reaction mixture was partitioned between ethyl acetate (75 mL) and half-saturated aqueous ammonium chloride (75 mL). The organic layer was washed with saturated aqueous NaCl (25 mL), dried (MgSO$_4$), filtered, and evaporated to an oil. The crude alcohol thus obtained was dissolved in benzene (20 mL) and p-toluenesulfonic acid (0.095 g, 0.5 mmol) was added. The resulting mixture was stirred at 80° C. for 2 hours then diluted with ethyl acetate (50 mL) and washed with 5% aqueous NaHCO$_3$ (50 mL). The organic layer was dried (K$_2$CO$_3$), filtered, and evaporated to a cream colored solid. The material thus obtained was purified by flash chromatography on silica gel eluted with 99:1 hexane:acetone then further purified by preparative thin layer chromatography on silica gel eluted with 4:1 hexane: dichloromethane to afford the product as a light yellow solid.

Step 4: Boron tribromide (0.208 mL of a 1.0 M solution of BBr$_3$ in dichloromethane, 0.21 mmol) was added to a cold (ice bath) solution of the product of step 3 (0.045 g, 0.14 mmol) in dichloromethane (2 mL). The ice bath was removed and the resulting dark brown solution was stirred at room temperature for 2 hours. The reaction mixture was then cooled in ice and added dropwise to a rapidly stirring mixture of ethyl acetate (25 mL) and 5% aqueous NaHCO$_3$ (25 mL). The aqueous layer was extracted with ethyl acetate (15 mL) and the combined organic layers were dried (MgSO$_4$), filtered, and evaporated to a yellow oil. The crude phenol thus obtained was purified by preparative thin layer chromatography on silica gel eluted with 9:1 hexane:acetone to afford 2-phenyl-5-hydroxy-1', 3'-dihydro-spiro[1H-indene-1,2'-[2H]indene] as a white amorphous solid. NMR (CDCl$_3$, 400 MHz) δ 7.5–7.6 (2H, m, ArH), 7.25–7.37 (7H, m, ArH), 7.19 (1H, s, olefin H), 6.88 (1H, d, J=2.5 Hz, ArH), 6.83 (1H, d, J=8 Hz, ArH), 6.53 (1H, dd, J=2.5, 8 Hz, ArH), 4.70 (1H, br s, OH), 3.75 (2H, d, J=16.5 Hz, ArCH$_2$), 3.13 (2H, d, J=16.5 Hz, ArCH$_2$). MS (electrospray): m/e 311 (M+H), 333 (M+Na).

EXAMPLE 2

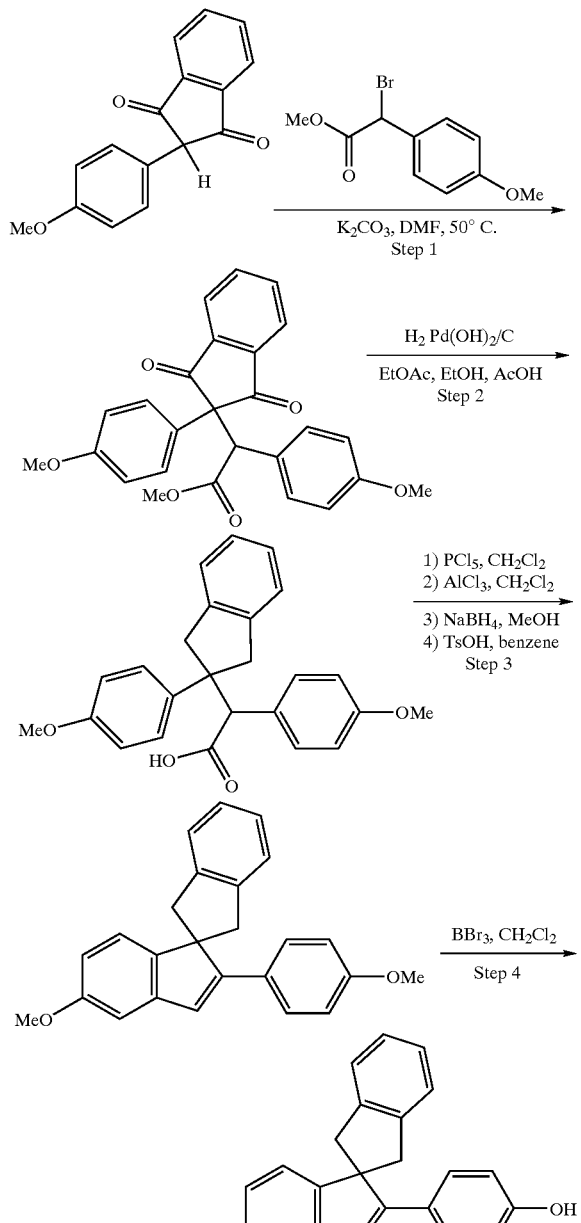

2-(4-Hydroxyphenyl)-5-hydroxy-1',3'-dihydro-spiro [1H-indene-1,2'-[2H]indene]

Step 1: Potassium carbonate (1.38 g, 10 mmol) was added to a solution of anisindione (2.02 g, 8 mmol) in dry dimethylformamide (35 mL). The resulting dark red mixture was stirred at room temperature for 10 minutes then a solution of methyl-α-bromo-4-methoxy-phenylacetate (2.59 g, 10 mmol) in dimethylformamide (5 mL) was added. The resulting mixture was stirred at 50° C. for 15 minutes then partitioned between half-saturated aqueous ammonium chloride (400 mL) and ethyl acetate (250 mL). The aqueous layer was extracted with ethyl acetate (50 mL) and the combined organic layers were dried (MgSO$_4$), filtered, and evaporated to an orange oil. The crude product was purified by flash chromatography on silica gel eluted with 3:1 hexane:ethyl acetate to afford the product as a light orange solid.

Step 2: Glacial acetic acid (2 mL) was added to a solution of the product of step 1 (3.44 g, 8 mmol) in 100 mL of 1:1 ethyl acetate:ethanol then 20% palladium hydroxide on carbon (344 mg) was added. The reaction vessel was evacuated and filled twice with nitrogen gas then evacuated and filled twice with hydrogen gas and stirred under an atmosphere of hydrogen gas (balloon) for 22.5 hours. The reaction mixture was then diluted with ethyl acetate (50 mL) and filtered through Celite®. The Celite® was washed with ethyl acetate (2×25 mL) and the combined filtrates were evaporated to an off-white foam. This material was purified by flash chromatography on silica gel eluted with 1% formic acid in 3:1 hexane:ethyl acetate to afford the product as a white foam.

Step 3: Phosphorus pentachloride (0.25 g, 1.2 mmol) was added in two equal portions to a cold (ice bath) solution of the product of step 2 (0.3885 g, 1.0 mmol) in dichloromethane (10 mL). The resulting mixture was stirred at 0° C. for 1 hour then then diluted by addition of dichloromethane (90 mL) and cooled to −20° C. Aluminum chloride (0.167 g, 1.25 mmol) was added and the resulting dark yellow solution was stirred at −20° C. for 1 hour then the temperature was increased to 0° C. and the reaction mixture was stirred at 0° C. for 75 minutes. Water (50 mL) was added (color changed to red then colorless) followed by chloroform (25 mL). The organic layer was washed sequentially with 5% aqueous NaHCO$_3$ (50 mL) and saturated aqueous NaCl (25 mL) then dried (MgSO$_4$/K$_2$CO$_3$), filtered, and evaporated to a light yellow solid. The crude ketone thus obtained was dissolved in 20 mL of 1:1 tetrahydrofuran:methanol then cooled in an ice bath as sodium borohydride (0.189 g, 5 mmol) was added slowly in small portions (CAUTION: vigorous reaction, gas evolution). The resulting mixture was stirred at room temperature for 75 minutes then additional sodium borohydride (0.090 g, 2.5 mmol) was added. After an additional 75 minutes at room temperature the reaction mixture was partitioned between ethyl acetate (75 mL) and half-saturated aqueous ammonium chloride (75 mL). The aqueous layer was extracted with ethyl acetate (25 mL) and the combined organic layers were washed with saturated aqueous NaCl (25 mL), dried (MgSO$_4$), filtered, and evaporated to a light yellow solid. The crude alcohol thus obtained was dried by evaporation from toluene then dissolved in benzene (20 mL) and p-toluenesulfonic acid (0.095 g, 0.5 mmol) was added. The resulting mixture was stirred at 80° C. for 2 hours then diluted with ethyl acetate (60 mL) and washed with 5% aqueous NaHCO$_3$ (2×50 mL). The organic layer was dried (MgSO$_4$/K$_2$CO$_3$), filtered, and evaporated to a bright yellow solid. The material thus obtained was purified by flash chromatography on silica gel eluted with 97:3 hexane:ethyl acetate then further purified by preparative thin layer chromatography on silica gel eluted with 1:1 hexane:benzene to afford the pure product as a light yellow solid.

Step 4: Boron tribromide (0.378 mL of a 1.0 M solution of BBr$_3$ in dichloromethane, 0.38 mmol) was added to a cold (ice bath) solution of the product of step 3 (0.045 g, 0.13 mmol) in dichloromethane (2 mL). The ice bath was removed and the resulting dark purple-red solution was stirred at room temperature for 2 hours. The deep purple reaction mixture was then cooled in ice and added dropwise to a rapidly stirring mixture of ethyl acetate (30 mL) and 5% aqueous NaHCO$_3$ (25 mL). The aqueous layer was extracted with ethyl acetate (15 mL) and the combined organic layers were dried (MgSO$_4$), filtered, and evaporated to a yellow-brown oil. The crude phenol thus obtained was purified by preparative thin layer chromatography on silica gel eluted with 4:1 hexane:ethyl acetate to afford 2-(4-hydroxyphenyl)-5-hydroxy-1',3'-dihydro-spiro[1H-indene-1,2'-[2H]indene] as a white amorphous solid. NMR (CDCl$_3$, 400 MHz) δ 7.36 (2H, d, J=9 Hz, ArH), 7.22–7.30 (4H, m, ArH), 6.99 (1H, s, olefin H), 6.81 (1H, d, J=2 Hz, ArH), 6.77 (2H, d, J=9 Hz, ArH), 6.75 (1H, d, J=8 Hz, ArH), 6.46 (1H, dd, J=2, 8 Hz, ArH), 6.14 (1H, br s, OH), 5.54 (1H, br s, OH), 3.65 (2H, d, J=16.5 Hz, ArCH$_2$), 3.07 (2H, d, J=16.5 Hz, ArCH$_2$). MS (electrospray): m/e 327 (M+H), 349 (M+Na).

EXAMPLE 3

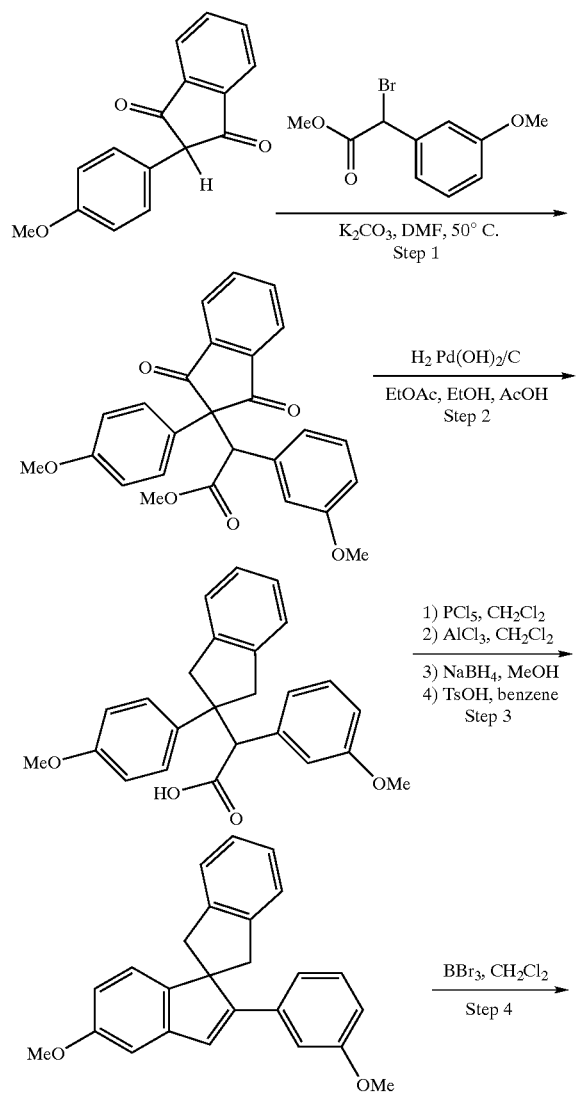

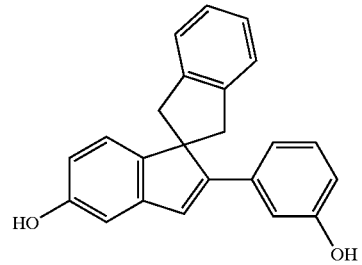

2-(3-Hydroxyphenyl)-5-hydroxy-1',3'-dihydro-spiro[1H-indene-1,2'-[2H]indene]

Step 1: Potassium carbonate (0.617 g, 4.46 mmol) was added to a solution of anisindione (0.90 g, 3.57 mmol) in dry dimethylformamide (16 mL). The resulting dark red mixture was stirred at room temperature for 10 minutes then a solution of methyl-α-bromo-3-methoxy-phenylacetate (1.11 g, 4.28 mmol) in dimethylformamide (4 mL) was added. The resulting mixture was stirred at 50° C. for 20 minutes then partitioned between half-saturated aqueous ammonium chloride (200 mL) and ethyl acetate (100 mL). The aqueous layer was extracted with ethyl acetate (50 mL) and the combined organic layers were dried (MgSO$_4$), filtered, and evaporated to an orange oil. The crude product was purified by flash chromatography on silica gel eluted with 3:1 hexane:ethyl acetate to afford the product as a light orange solid.

Step 2: Glacial acetic acid (1 mL) was added to a solution of the product of step 1 (1.34 g, 3.11 mmol) in 50 mL of 1:1 ethyl acetate:ethanol then 20% palladium hydroxide on carbon (175 mg) was added. The reaction vessel was evacuated and filled twice with nitrogen gas then evacuated and filled twice with hydrogen gas and stirred under an atmosphere of hydrogen gas (balloon) for 39 hours. The reaction mixture was then diluted with ethyl acetate (25 mL) and filtered through Celite®. The Celite® was washed with ethyl acetate (2×10 mL) and the combined filtrates were evaporated to a yellow oil. This material was purified by recrystallization from hexane/ethyl acetate to afford the product as a white solid (mp 130–131° C.).

Step 3: Phosphorus pentachloride (0.25 g, 1.2 mmol) was added in two equal portions to a cold (ice bath) solution of the product of step 2 (0.389 g, 1.0 mmol) in dichloromethane (10 mL). The resulting mixture was stirred at 0° C. for 1 hour then then diluted by addition of dichloromethane (90 mL). Aluminum chloride (0.167 g, 1.25 mmol) was added and the resulting mixture was stirred at 0° C. for 90 minutes. Water (50 mL) was then added followed by chloroform (25 mL). The organic layer was washed sequentially with 5% aqueous NaHCO$_3$ (50 mL) and saturated aqueous NaCl (25 mL) then dried (MgSO$_4$/K$_2$CO$_3$), filtered, and evaporated to a light yellow solid. The crude ketone thus obtained was dissolved in 20 mL of 1:1 tetrahydrofuran:methanol then cooled in an ice bath as sodium borohydride (0.190 g, 5 mmol) was added slowly in small portions (CAUTION: vigorous reaction, gas evolution). The resulting mixture was stirred at room temperature for 1 hour then additional sodium borohydride (0.090 g, 2.5 mmol) was added. After an additional 1 hour at room temperature the reaction mixture was partitioned between ethyl acetate (75 mL) and half-saturated aqueous ammonium chloride (75 mL). The aqueous layer was extracted with ethyl acetate (25 mL) and the combined organic layers were washed with saturated aqueous NaCl (25 mL), dried (MgSO₄), filtered, and evaporated to a yellow solid. The crude alcohol thus obtained was dissolved in benzene (20 mL) and p-toluenesulfonic acid (0.095 g, 0.5 mmol) was added. The resulting mixture was stirred at 80° C. for 2 hours then diluted with ethyl acetate (80 mL) and washed with 5% aqueous NaHCO₃ (2×50 mL). The organic layer was dried (MgSO₄/K₂CO₃), filtered, and evaporated to a bright yellow solid. The material thus obtained was purified by flash chromatography on silica gel eluted with 97:3 hexane:ethyl acetate then further purified by preparative thin layer chromatography on silica gel eluted with 1:1 hexane:benzene to afford the pure product as a colorless oil.

Step 4: Boron tribromide (0.189 mL of a 1.0 M solution of BBr₃ in dichloromethane, 0.19 mmol) was added to a cold (ice bath) solution of the product of step 3 (0.022 g, 0.06 mmol) in dichloromethane (2 mL). The ice bath was removed and the resulting amber solution was stirred at room temperature for 2 hours. The reaction mixture was then cooled in ice and added dropwise to a rapidly stirring mixture of ethyl acetate (30 mL) and 5% aqueous NaHCO₃ (25 mL). The aqueous layer was extracted with ethyl acetate (15 mL) and the combined organic layers were dried (MgSO₄), filtered, and evaporated to an oil. The crude phenol thus obtained was purified by preparative thin layer chromatography on silica gel eluted with 4:1 hexane:ethyl acetate to afford 2-(3-hydroxyphenyl)-5-hydroxy-1',3'-dihydro-spiro[1H-indene-1,2'-[2H]indene] as a white amorphous solid. NMR (CDCl₃, 400 MHz) δ 7.24–7.32 (4H, m, ArH), 7.17 (1H, t, J=8 Hz, ArH), 7.11 (1H, s, olefin H), 7.07 (1H, br d, J=8 Hz, ArH), 6.92 (1H, t, J=2 Hz, ArH), 6.83 (1H, d, J=4 Hz, ArH), 6.78 (1H, d, J=8 Hz, ArH), 6.72 (1H, dd, J=2, 8 Hz, Ar), 6.49 (1H, dd, J=2, 8 Hz, ArH), 4.91 (1H, br s, OH), 4.72 (1H, br s, OH), 3.69 (2H, d, J=16.5 Hz, ArCH₂), 3.10 (2H, d, J=16.5 Hz, ArCH₂). MS (electrospray): m/e 327 (M+H), 349 (M+Na).

EXAMPLE 4

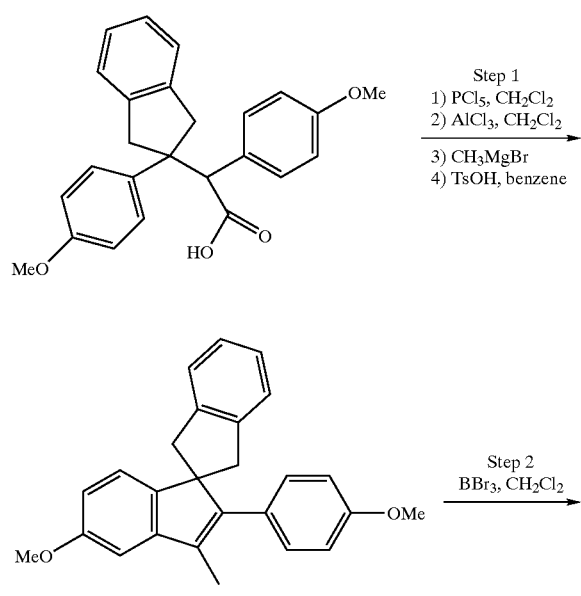

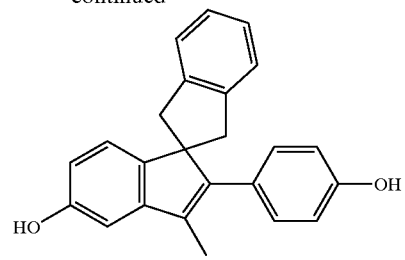

2-(4-Hydroxyphenyl)-3-methyl-5-hydroxy-1',3'-dihydro-spiro[1H-indene-1,2'-[2H]indene]

Step 1: Phosphorus pentachloride (0.25 g, 1.2 mmol) was added in two equal portions to a cold (ice bath) solution of the product of step 2 of Example 2 (0.389 g, 1.0 mmol) in dichloromethane (10 mL). The resulting mixture was stirred at 0° C. for 1 hour then diluted by addition of dichloromethane (90 mL). Aluminum chloride (0.167 g, 1.25 mmol) was added and the resulting mixture was stirred at 0° C. for 75 minutes (color changed to red-orange). Water (50 mL) was added followed by chloroform (25 mL). The organic layer was washed sequentially with 5% aqueous NaHCO₃ (50 mL) and saturated aqueous NaCl (25 mL) then dried (MgSO₄/K₂CO₃), filtered, and evaporated to a yellow solid. The crude ketone thus obtained was dissolved in dry tetrahydrofuran (10 mL). Methylmagnesium chloride (1.67 mL of 3 M solution in tetrahydrofuran, 5 mmol) was added (reaction mildly exothermic). The resulting solution was stirred at room temperature for 90 minutes then partitioned between ethyl acetate (50 mL) and half-saturated aqueous ammonium chloride (50 mL). The aqueous layer was extracted with ethyl acetate (25 mL) and the combined organic layers were washed with saturated aqueous NaCl (25 mL), dried (MgSO₄), filtered, and evaporated to an orange solid. The crude tertiary alcohol thus obtained was dissolved in benzene (20 mL) and p-toluenesulfonic acid (0.095 g, 0.5 mmol) was added. The resulting mixture was stirred at 80° C. for 2.5 hours then diluted with ethyl acetate (60 mL) and washed with 5% aqueous NaHCO₃ (2×50 mL). The organic layer was dried (MgSO₄/K₂CO₃), filtered, and evaporated to an orange-brown solid. The material thus obtained was purified by flash chromatography on silica gel eluted with 97:3 hexane:ethyl acetate then further purified by preparative thin layer chromatography on silica gel eluted with 1:1 hexane:benzene to afford the pure product as a light yellow solid.

Step 2: Boron tribromide (0.171 mL of a 1.0 M solution of BBr₃ in dichloromethane, 0.17 mmol) was added to a cold (ice bath) solution of the product of step 1 (0.021 g, 0.057 mmol) in dichloromethane (2 mL). The ice bath was removed and the resulting dark brown solution was stirred at room temperature for 2 hours. The deep purple reaction mixture was then cooled in ice and added dropwise to a rapidly stirring mixture of ethyl acetate (30 mL) and 5% aqueous NaHCO₃ (25 mL). The aqueous layer was extracted with ethyl acetate (15 mL) and the combined organic layers were dried (MgSO₄), filtered, and evaporated to a yellow oil. The crude phenol thus obtained was purified by preparative thin layer chromatography on silica gel eluted with 4:1 hexane:ethyl acetate to afford 2-(4-hydroxyphenyl)-3-methyl-5-hydroxy-1',3'-dihydro-spiro[1H-indene-1,2'-[2H]indene] as a white amorphous solid. NMR (CDCl₃, 400 MHz) δ 7.06–7.14 (4H, m, ArH), 6.99 (2H, d, J=9 Hz, ArH), 6.79 (2d, J=9 Hz, ArH), 6.76 (1H, d, J=2 Hz, ArH), 6.71 (1H, br s, OH), 6.62 (1H, d, J=8 Hz, ArH), 6.44 (1H, dd, J=2, 8 Hz, ArH), 6.30 (1H, br s, OH), 3.40 (2H, d, =15.5 Hz, ArCH$_2$), 2.84 (2H, d, J=16.5 Hz, ArCH$_2$), 1.90 (3H, s, CH$_3$). MS (electrospray): m/e 341 (M+H), 363 (M+Na).

EXAMPLE 5

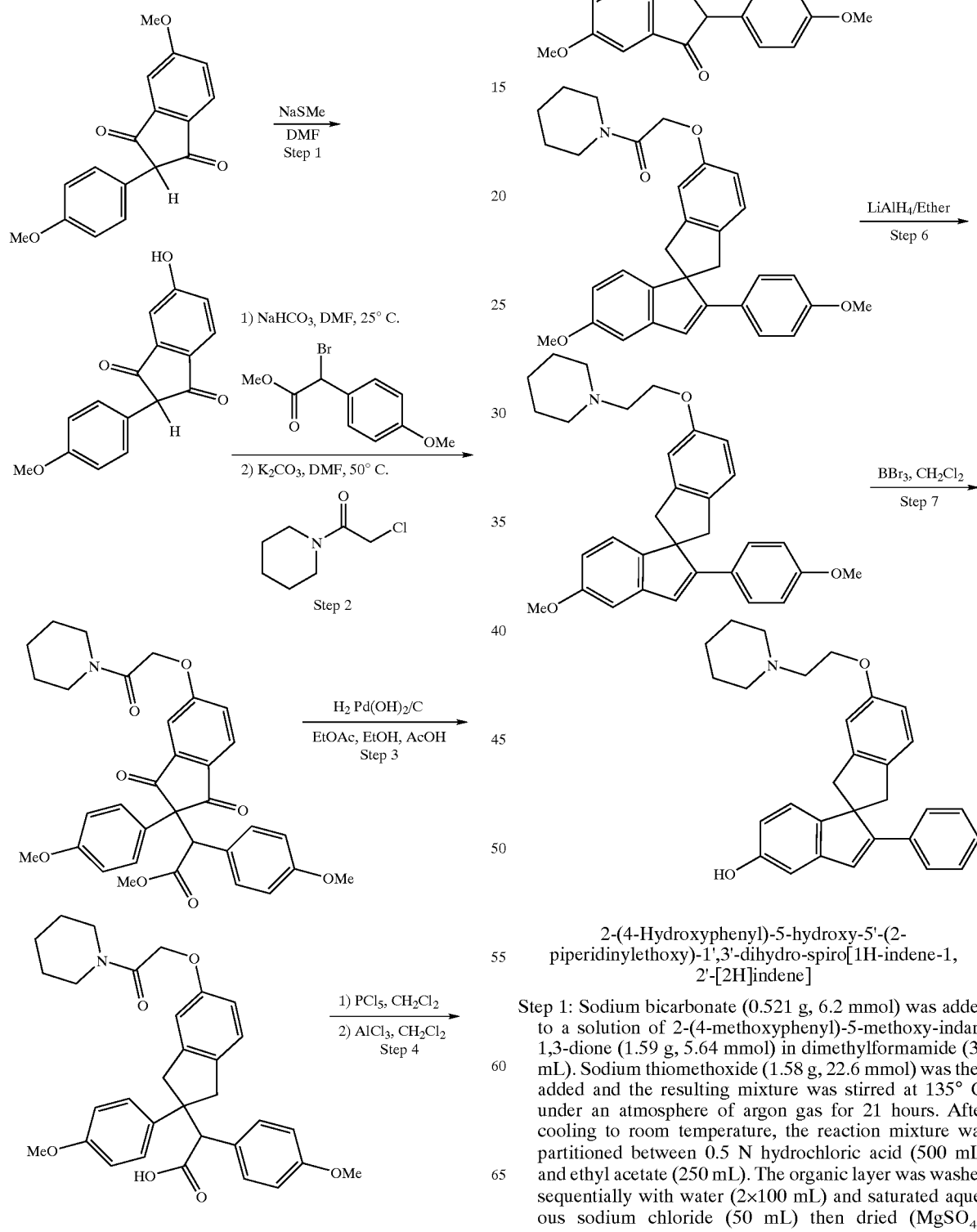

2-(4-Hydroxyphenyl)-5-hydroxy-5'-(2-piperidinylethoxy)-1',3'-dihydro-spiro[1H-indene-1, 2'-[2H]indene]

Step 1: Sodium bicarbonate (0.521 g, 6.2 mmol) was added to a solution of 2-(4-methoxyphenyl)-5-methoxy-indan-1,3-dione (1.59 g, 5.64 mmol) in dimethylformamide (30 mL). Sodium thiomethoxide (1.58 g, 22.6 mmol) was then added and the resulting mixture was stirred at 135° C. under an atmosphere of argon gas for 21 hours. After cooling to room temperature, the reaction mixture was partitioned between 0.5 N hydrochloric acid (500 mL) and ethyl acetate (250 mL). The organic layer was washed sequentially with water (2×100 mL) and saturated aqueous sodium chloride (50 mL) then dried (MgSO$_4$), filtered, and evaporated to an orange oil (2.13 g). The crude phenol thus obtained was purified by flash chromatography on silica gel eluted with 97.5:2.5 dichloromethane:methanol to afford 5-hydroxy-2-(4-methoxyphenyl)-1-indene-1,3(2H)-dione as a light orange amorphous solid.

Step 2: Sodium bicarbonate (0.327 g, 3.9 mmol) was added to a solution of the product of step 1 (0.87 g, 3.25 mmol) in anhydrous dimethylformamide (15 mL). The resulting solution was stirred at room temperature for 5 minutes then a solution of methyl alpha-bromo-4-methoxyphenylacetate (0.883 g, 3.4 mmol) in anhydrous dimethylformamide (1.25 mL) was added. The resulting solution was stirred at room temperature for 1 hour then additional sodium bicarbonate (0.035 g, 0.4 mmol) and methyl alpha-bromo-4-methoxyphenylacetate (0.075 g, 0.3 mmol; solution in 0.5 mL of dimethylformamide) were added. The reaction mixture was stirred at room temperature for an additional hour then powdered potassium carbonate (0.539 g, 3.9 mmol) was added. The resulting mixture was stirred at room temperature for 5 minutes then a solution of N-chloroacetyl piperidine (0.578 g, 3.6 mmol) in anhydrous dimethylformamide (1 mL) was added. The resulting mixture was stirred at 55–60° C. for 3 hours then cooled to room temperature and partitioned between water (300 mL) and ethyl acetate (300 mL). The organic layer was washed sequentially with water (100 mL) and saturated aqueous sodium chloride (100 mL) then dried (MgSO$_4$), filtered, and evaporated to an straw-colored solid. The crude product thus obtained was purified by flash chromatography on silica gel eluted with 98.5:1.5 dichloromethane:methanol to afford the title compound as an off-white amorphous solid.

Step 3: Glacial acetic acid (5 mL) was added to a solution of the product of step 2 (1.50 g, 2.6 mmol) in 1:1 ethyl acetate:ethanol (100 mL). The resulting solution was treated with activated charcoal and filtered through Celite® (Celite® was washed with 1:1 ethyl acetate:ethanol (25 mL)). Glacial acetic acid (2 mL) was added to the filtrate then 20% palladium hydroxide on carbon (0.500 g) was added. The reaction vessel was evacuated and filled with nitrogen then evacuated and filled with hydrogen and the reaction mixture was stirred under a hydrogen atmosphere (balloon) for 108 hours (additional catalyst (0.250 g) was added twice (after 17 and 39 hours)). The reaction mixture was filtered through Celite® (Celite® was washed with ethyl acetate) and the filtrate was concentrated under vacuum. The residue was dissolved in toluene and evaporated (twice) to afford a yellow oil. The crude product thus obtained was purified by flash chromatography on silica gel eluted with 1% formic acid in 6:4 hexane:acetone to afford the title compound as a white solid.

Step 4: Phosphorus pentachloride (0.165 g, 0.79 mmol) was added in two portions to a cold (0° C.) solution of the product of step 3 (0.35 g, 0.66 mmol) in anhydrous dichloromethane (10 mL). The resulting solution was stirred at 0° C. for 90 minutes then additional phosphorus pentachloride (0.25 g, 0.12 mmol) was added. The resulting solution was stirred at 0° C. for an additional 30 minutes then diluted with dichloromethane (90 mL). Aluminum chloride (0.127 g, 0.96 mmol) was added and the resulting mixture was stirred at 0° C. for 90 minutes then the cold bath was removed and the reaction mixture was stirred at room temperature for 2.5 hours. TLC analysis of the reaction mixture indicated that little, if any, reaction had occurred so the reaction mixture was re-cooled to 0° C. and additional aluminum chloride (0.100 g, 0.76 mmol) was added. The cold bath was again removed and the reaction mixture was stirred at room temperature for 45 minutes (TLC showed reaction complete). The reaction mixture was cooled in an ice-bath as water (100 mL) and chloroform (50 mL) were added. The organic layer was washed sequentially with 5% aqueous sodium bicarbonate (100 mL) and saturated aqueous sodium chloride (50 mL) then dried (MgSO$_4$/K$_2$CO$_3$), filtered, and evaporated to an oil. The crude product thus obtained was purified by flash chromatography on silica gel eluted with 3:1 hexane:acetone to afford the pure product as a white solid.

Step 5: Sodium borohydride (0.030 g, 0.78 mmol) was added in two portions to a cold (0° C.) solution of the product of step 4 (0.080 g, 0.156 mmol) in 1:1 tetrahydrofuran:methanol (4 mL). The cold bath was removed and the resulting solution was stirred at room temperature for 75 minutes. Additional sodium borohydride (0.015 g, 0.39 mmol) was added and the reaction mixture was stirred at room temperature for an additional 45 minutes. The reaction mixture was then partitioned between ethyl acetate (25 mL) and pH 6 aqueous buffer solution (25 mL). The aqueous layer was extracted with ethyl acetate (10 mL). The combined organic layers were washed with saturated aqueous sodium chloride (15 mL), dried (MgSO$_4$), filtered, and evaporated to an oil. The intermediate alcohol thus obtained was evaporated twice from toluene solution then dissolved in anhydrous benzene (10 mL). p-Toluenesulfonic acid (0.010 g, 0.052 mmol) was added and the resulting solution was stirred at 80° C. for 1.75 hours. The reaction mixture was cooled to room temperature, diluted with ethyl acetate (25 mL), and washed sequentially with 5% aqueous sodium bicarbonate (20 mL) and saturated aqueous sodium chloride (15 mL) then dried (MgSO$_4$), filtered, and evaporated to an orange oil. The crude product thus obtained was purified by flash chromatography on silica gel eluted with 7:3 hexane: acetone to afford the title compound as a light orange oil.

Step 6: Lithium aluminum hydride (0.006 g, 0.16 mmol) was added to a solution of the product of step 5 (0.040 g, 0.08 mmol) in anhydrous ether (3 mL). The resulting mixture was stirred at 30–35° C. for 2.25 hours then partitioned between ethyl acetate (25 mL) and 0.5 N aqueous sodium hydroxide (15 mL). The aqueous layer was extracted with ethyl acetate (10 mL) and the combined organic layers were dried (MgSO$_4$), filtered, and evaporated to a light orange oil. The crude product thus obtained was sufficiently pure for use in the next step without further purification.

Step 7: Boron tribromide (0.156 mL of 1 M solution in dichloromethane, 0.156 mmol) was added to a cold (0° C.) solution of the product of step 6 (0.025 g, 0.052 mmol) in anhydrous dichloromethane (2 mL). The cold bath was removed and the solution was stirred at room temperature for 90 minutes. The reaction mixture was then added dropwise to a cold (0° C.), rapidly stirring, mixture of 5% aqueous sodium bicarbonate (25 mL) and ethyl acetate (25 mL). After separating the layers, the pH of the aqueous layer was adjusted to ~9.5 by addition of 0.5 N aqueous sodium hydroxide then the aqueous layer was extracted with ethyl acetate (15 mL). The combined organic layers were dried (MgSO$_4$), filtered, and evaporated to a yellow solid. The crude product was purified by flash chromatography on silica gel eluted with 1% triethyl amine in 1:1 hexane:acetone to afford 2-(4-hydroxyphenyl)-5-hydroxy-5'-(2-piperidinylethoxy)-1',3'-dihydro-spiro[1H-indene-1,2'-[2H]indene] as an off-white amorphous solid (0.003 g). NMR (acetone-$d_6$, 400 MHz) δ 7.41 (2H, d, J=9 Hz, ArH), 7.21 (1H, d, J=8 Hz, ArH), 7.09 (1H, s, olefin H), 6.92 (1H, br d, J=2 Hz, ArH), 6.85 (1H, dd, J=2, 8 Hz, ArH), 6.82 (1H, d, J=2 Hz, ArH), 6.80 (2H, d, J=9 Hz, ArH), 6.72 (1H, d, J=8 Hz, ArH), 6.49 (1H, dd, J=2, 8 Hz, ArH), 4.11 (2H, t, J=6 Hz, OCH$_2$), 3.61 (1H, d, J=16.5 Hz, ArCH$_2$), 3.56 (1H, d, J=16 Hz, ArCH$_2$), 2.98 (1H, d, J=16.5 Hz, ArCH$_2$), 2.95 (1H, d, J=16 Hz, ArCH$_2$), 2.71 (2H, t, J=6 Hz, NCH$_2$), 2.48 (4H, br s, NCH$_2$), 1.54 (4H, m, CH$_2$), 1.41 (2H, m, CH$_2$). MS (electrospray): m/e 454 (M+H).

EXAMPLE 6

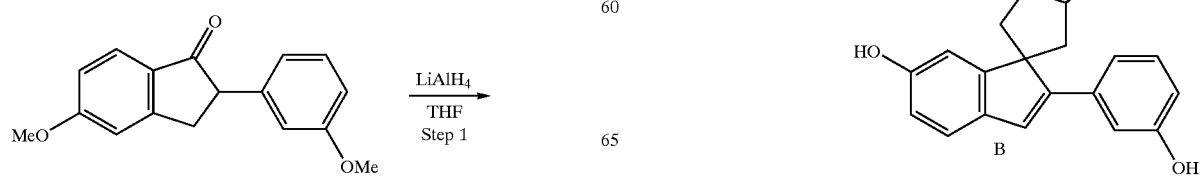

2-Phenyl-1',3'-dihydro-spiro[1H-indene-1,2'-[2H]indene]

Benzyl trimethylammonium chloride (0.196 g, 1 mmol) was added to a solution of 2-phenylindene (0.200 g, 1.04 mmol) and α,α'-dibromoxylene (0.289 g, 1.09 mmol) in tetrahydrofuran (10 mL) then 50% aqueous sodium hydroxide (10 mL) was added. The resulting mixture was stirred at 50° C. overnight. The reaction mixture was partitioned between ethyl acetate and water. The organic layer was washed sequentially with water, 0.1 N hydrochloric acid, water, and saturated aqueous sodium chloride then dried (MgSO$_4$), filtered, and evaporated to a yellow solid. The crude product was purified by preparative thin layer chromatography on silica gel eluted with 98:2 hexane:ethyl acetate to afford 2-phenyl-1',3'-dihydro-spiro[1H-indene-1,2'-[2H]indene] as a white amorphous solid (0.048 g). NMR (CDCl$_3$, 500 MHz) δ 7.56 (2H, d, J=7 Hz), 7.42 (1H, d, J=7 Hz), 7.24–7.38 (9H, m, ArH), 7.09 (1H, t, J=7 Hz, ArH), 7.02 (1H, d, J=7 Hz, ArH), 3.78 (2H, d, J=16.5 Hz, CH$_2$), 3.19 (2H, d, J=16.5 Hz, CH$_2$).

EXAMPLE 7

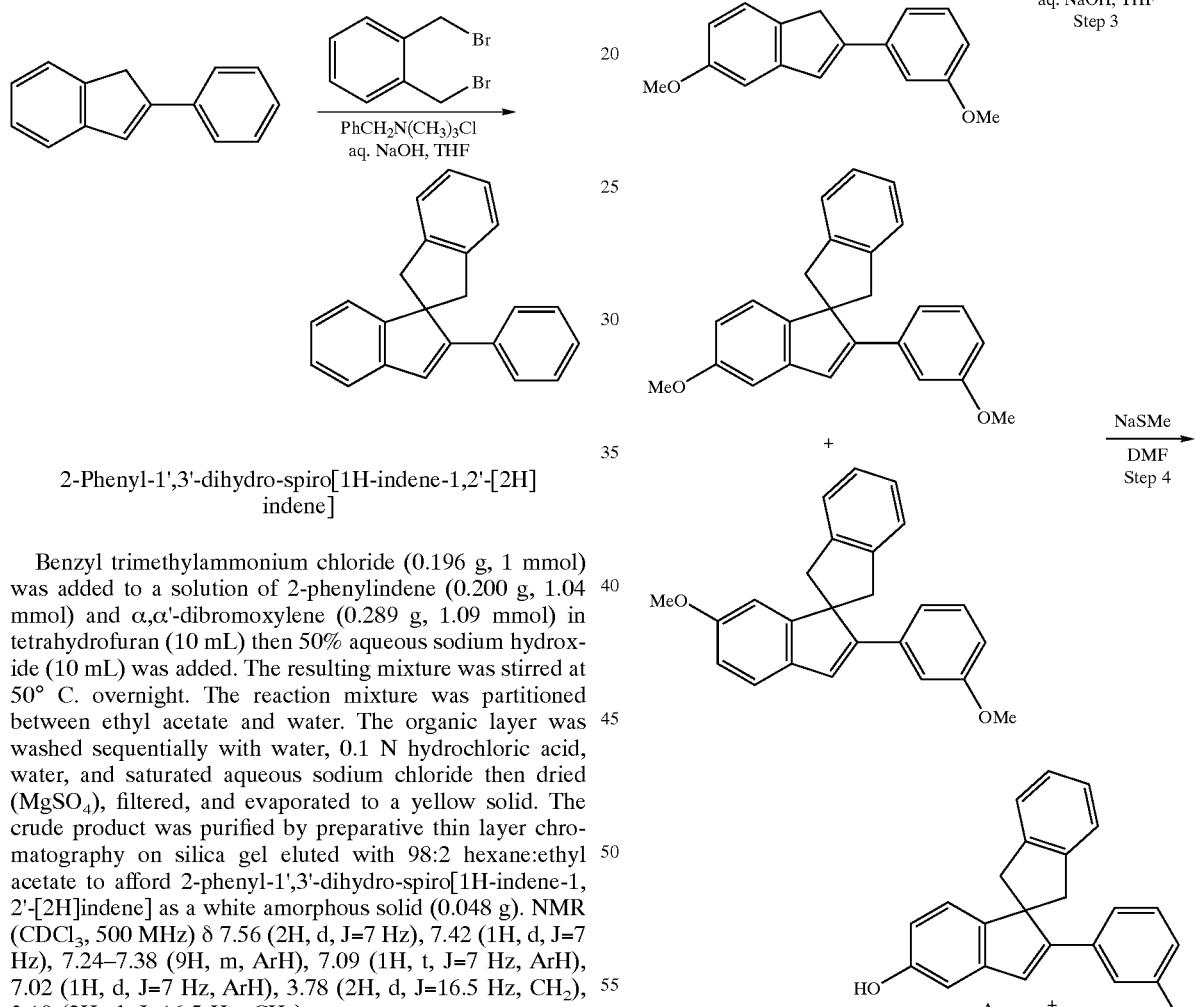

2-(3-Hydroxyphenyl)-5-hydroxy-1',3'-dihydro-spiro[1H-indene-1,2'-[2H]indene] (A) and 2-(3-hydroxyphenyl)-6-hydroxy-1',3'-dihydro-spiro[1H-indene-1,2'-[2H]indene] (B)

Step 1: Lithium aluminum hydride (1.68 g, 44.3 mmol) was added to a solution of 2-(3-methoxyphenyl)-5-methoxy-indan-1-one (4.0 g, 14.9 mmol) in anhydrous tetrahydrofuran (68 mL). The resulting mixture was stirred at room temperature over the weekend. The reaction mixture was then cooled in an ice bath as water (5.1 mL), 15% aqueous sodium hydroxide (5.1 mL), and water (1.7 mL) were added sequentially. The resulting mixture was sonicated and filtered. The filtrate was dried (MgSO$_4$), filtered, and evaporated to an oil. The crude product thus obtained was sufficiently pure for use in the next step without further purification.

Step 2: The crude product obtained in step 1 (3.98 g, 14.7 mmol) was dissolved in anhydrous benzene (100 mL) then p-toluenesulfonic acid (1.4 g, 7.35 mmol) was added. The resulting mixture was refluxed for 3.5 hours then concentrated under vacuum. The residue was partitioned between ethyl acetate and water. The organic layer was washed twice with saturated aqueous sodium bicarbonate then dried (MgSO$_4$), filtered, and evaporated to an oil. The crude product was purified by flash chromatography on silice gel eluted with 6:1 hexane:ethyl acetate to afford the pure product as a mixture of olefin regio-isomers.

Step 3: Benzyl trimethylammonium chloride (0.346 g, 1.83 mmol) was added to a solution of the olefin isomer mixture obtained as the product of step 2 (0.40 g, 1.59 mmol) and α,α'-dibromoxylene (0.44 g, 1.67 mmol) in tetrahydrofuran (16 mL) then 50% aqueous sodium hydroxide (16 mL) was added. The resulting mixture was stirred at 50° C. over the weekend. The reaction mixture was partitioned between ethyl acetate and water. The organic layer was washed sequentially with water and saturated aqueous sodium chloride then dried (MgSO$_4$), filtered, and evaporated to a yellow solid. The crude product was purified by preparative thin layer chromatography on silica gel to afford the product as a mixture of regioisomers.

Step 4: The mixture of regioisomers obtained as the product of step 3 (0.175 g, 0.49 mmol) was dissolved in dimethylformamide (14 mL). Sodium thiomethoxide (0.95 g, 13.6 mmol) was added and the resulting mixture was stirred under an Argon atmosphere at 100° C. for 13.75 hours. Additional sodium thiomethoxide was then added and stirring continued at 100° C. for an additional 3 hours. The reaction mixture was partitioned between ethyl acetate and water. The pH of the aqueous layer was adjusted to ~5.5 by addition of 2 N hydrochloric acid then the aqueous layer was extracted with ethyl acetate. The combined organic layers were washed sequentially with water and saturated aqueous sodium chloride then dried (MgSO$_4$), filtered, and evaporated to an oil. The crude product was purified by preparative thin layer chromatography on silica gel eluted with 4:1 hexane:ethyl acetate to afford the separated regioisomers A and B. Isomer A was found to be identical to the final product of Example 3. Isomer B was shown by NOE experiments to be the other isomer. NMR of isomer B (CDCl$_3$, 500 MHz) δ 7.18–7.40 (7H, m, ArH), 7.09 (1H, d, J=8 Hz, ArH), 6.98 (1H, t, J=2 Hz, ArH), 6.74 (2H, dd, J=2, 8 Hz, ArH), 6.49 (1H, d, J=7 Hz, ArH), 4.79 (1H, s, OH), 4.63 (1H, s, OH), 3.77 (2H, d, J=16.5 Hz, CH$_2$), 3.12 (2H, d, J=16.5 Hz, CH$_2$).

EXAMPLE 8

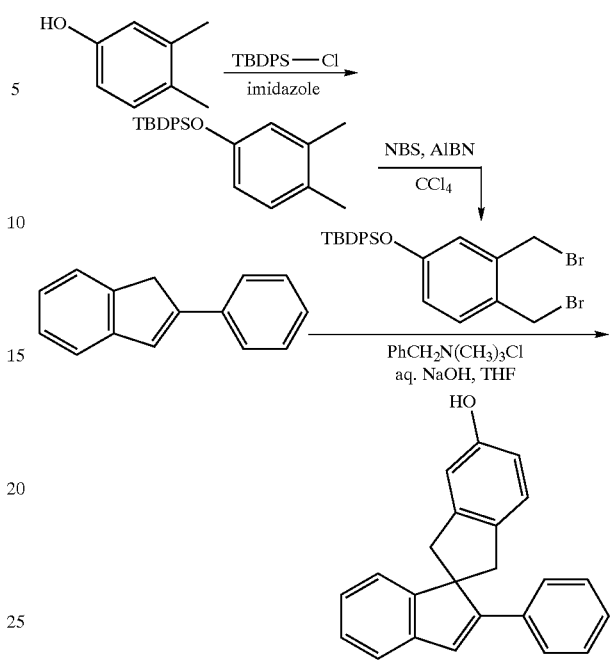

2-Phenyl-5'-hydroxy-1',3'-dihydro-spiro[1H-indene-1,2'-[2H]indene]

Step 1: t-Butyldiphenylsilylchloride (7.0 mL, 26.9 mmol) was added to a solution of 3,4-dimethylphenol (3.0 g, 24.6 mmol) and imidazole (3.69 g, 54.2 mmol) in anhydrous dimethylformamide (10 mL). The resulting mixture was stirred at room temperature overnight. The reaction mixture was then partitioned between ether and water. The organic layer was washed twice with water, then twice with saturated aqueous sodium bicarbonate, then once with saturated aqueous sodium chloride then dried over potassium carbonate, filtered, and concentrated under vacuum. The residue was purified by flash chromatography on silica gel eluted with 9:1 hexane:ethyl acetate to afford the pure product.

Step 2: The product of step 1 (3.45 g, 9.57 mmol), N-bromosuccinimide (3.58 g, 20.1 mmol), and 2,2'-azobis-isobutyronitrile (0.10 g, 0.6 mmol) were dissolved in carbon tetrachloride (29 mL) and the resulting mixture was refluxed for 4 hours. The mixture was then cooled to 50° C. and filtered (solid rinsed with carbon tetrachloride). The filtrate was evaporated to a yellow solid which was recrystallized from hexane to afford a white crystalline solid. This material was further purified by flash chromatography on silica gel eluted with 9:1 hexane:ethyl acetate to afford the product which was still not completely pure but which was judged to be of sufficient purity for the next step.

Step 3: Benzyl trimethylammonium chloride (0.126 g, 0.68 mmol) was added to a solution of 2-phenylindene (0.0.116 g, 0.6 mmol) and the dibromide (0.33 g, 0.64 mmol) obtained as the product of step 2 in tetrahydrofuran (6 mL) then 50% aqueous sodium hydroxide (6 mL) was added. The resulting mixture was stirred at 50° C. for 2 hours then partitioned between ethyl acetate and water. The organic layer was washed sequentially with water and saturated aqueous sodium chloride then dried (MgSO$_4$), filtered, and evaporated. The crude product was purified by preparative thin layer chromatography on silica gel eluted with 9:1 hexane:ethyl acetate to afford 2-phenyl- 5'-hydroxy-1',3'-dihydro-spiro[1H-indene-1,2'-[2H] indene]. NMR of isomer B (CDCl₃,500 MHz) 7.55 (2H, d, J=8 Hz, ArH), 7.41 (1H, d, J=7 Hz, ArH), 7.36 (2H, t, J=8 Hz, ArH), 7.24–7.31 (3H, m, ArH), 7.20 (1H, d, J=8 Hz, ArH), 7.10 (1H, t, J=7 Hz, ArH), 7.06 (H, d, J=7 Hz, ArH), 6.83 (1H, br s, olefin H), 6.81 (1H, dd, J=2, 8 Hz, ArH), 4.82 (1H, br s, OH), 3.71 (1H, d, J=15 Hz, CH₂), 3.68 (1H, d, J=15 Hz, CH₂), 3.11 (1H, d, J=15 Hz, CH₂), 3.09 (1H, d, J=15 Hz, CH₂).

Estrogen Receptor Binding Assay

The estrogen receptor ligand binding assays are designed as scintillation proximity assays employing the use of tritiated estradiol and recombinant expressed estrogen receptors. The full length recombinant human ER-α and ER-β proteins are produced in a bacculoviral expression system. ER-α or ER-β extracts are diluted 1:400 in phosphate buffered saline containing 6 mM α-monothiolglycerol. 200 μL aliquots of the diluted receptor preparation are added to each well of a 96-well Flashplate. Plates are covered with Saran Wrap and incubated at 4° C. overnight.

The following morning, a 20 ul aliquot of phosphate buffered saline containing 10% bovine serum albumin is added to each well of the 96 well plate and allowed to incubate at 4° C. for 2 hours. Then the plates are washed with 200 ul of buffer containing 20 mM Tris (pH 7.2), 1 mM EDTA, 10% Glycerol, 50 mM KCl, and 6 mM α-monothiolglycerol. To set up the assay in these receptor coated plates, add 178 ul of the same buffer to each well of the 96 well plate. Then add 20 ul of a 10 nM solution of ³H-estradiol to each well of the plate.

Test compounds are evaluated over a range of concentrations from 0.01 nM to 1000 nM. The test compound stock solutions should be made in 100% DMSO at 100× the final concentration desired for testing in the assay. The amount of DMSO in the test wells of the 96 well plate should not exceed 1%. The final addition to the assay plate is a 2 ul aliquot of the test compound which has been made up in 100% DMSO. Seal the plates and allow them to equilibrate at room temperature for 3 hours. Count the plates in a scintillation counter equipped for counting 96 well plates.

The compounds of Examples 1–111 exhibit binding affinities to the estrogen receptor α-subtype in the range of $IC_{50}$=2.8–5625 nm, and to the estrogen receptor β-subtype in the range of $IC_{50}$=0.6–126 nm.

Pharmaceutical Composition

As a specific embodiment of this invention, 25 mg of a compound of Example 1, is formulated with sufficient finely divided lactose to provide a total amount of 580 to 590 mg to fill a size 0, hard-gelatin capsule.

What is claimed is:

1. A compound of the formula:

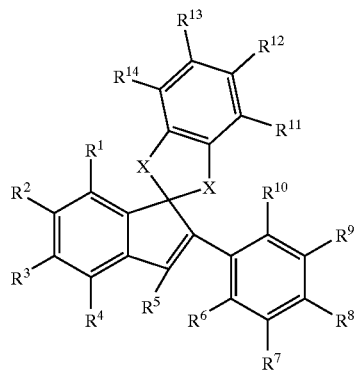

wherein each X is independently selected from the group consisting of $CH_2$, $C=O$, $C=CH_2$, $C=NOR^a$, $CHCH_3$, $CHF$, $CHOH$, $C(CH_3)OH$, $CF_2$ and S;

$R^1$, $R^2$, $R^3$, $R^4$, $R^6$, $R^7$, $R^8$, $R^9$ and $R^{10}$ are each independently selected from the group consisting of $R^a$, $OR^a$, $OCO_2R^a$, $NR^aR^a$, $CO_2R^a$, CN, Cl, F and Br;

$R^{11}$, $R^{12}$, $R^{13}$ and $R^{14}$ are each independently selected from the group consisting of H, $R^b$, $OR^b$, $OCO_2R^b$, $NR^aR^b$, $CO_2R^b$, F, Cl, CN, Br;

$R^5$ is selected from the group consisting of H, F and $C_{1-6}$alkyl;

$R^a$ is selected from the group consisting of H, $C_{1-6}$alkyl and $C_{1-6}$acyl;

$R^b$ is selected from the group consisting of $C_{2-7}$alkyl and $C_{2-7}$acyl, wherein said alkyl and acyl groups may be optionally substituted with an $R^c$ group;

$R^c$ is selected from the group consisting of $OR^d$ and $NR^dR^e$, $R^d$ and $R^e$ are each independently selected from the group consisting of H and $C_{1-7}$ alkyl;

or $R^d$ and $R^e$ can be taken together with the nitrogen atom to which they are attached to form a 4–8 membered ring, wherein said ring may be optionally interrupted by one of O, NH, $NCH_3$ and S and said ring may be optionally substituted with substituents selected from the group consisting of one, two, three or four $C_{1-2}$ alkyl groups, and one or two $R^f$ groups;

$R^f$ is selected from the group consisting of $CH_2OH$ and $CH_2CH_2OH$;

or a pharmaceutically acceptable salt or stereoisomer thereof.

2. The compound of claim 1 wherein each X is independently selected from the group consisting of $CH_2$ and $C=O$; or a pharmaceutically acceptable salt or stereoisomer thereof.

3. The compound of claim 2 wherein $R^1$, $R^2$, $R^3$, $R^4$, $R^6$, $R^7$, $R^8$, $R^9$ and $R^{10}$ are each independently selected from the group consisting of $R^a$, $OR^a$, Cl, F and Br; or a pharmaceutically acceptable salt or stereoisomer thereof.

4. The compound of claim 3 wherein $R^{11}$, $R^{12}$, $R^{13}$ and $R^{14}$ are each independently selected from the group consisting of H, $R^b$ and $OR^b$; or a pharmaceutically acceptable salt or stereoisomer thereof.

5. The compound of claim 4 wherein each X is $CH_2$; $R^1$, $R^6$, $R^9$, $R^{10}$, $R^{11}$, and $R^{12}$ are H;

$R^5$ is selected from the group consisting of H and $CH_3$;

$R^2$, $R^3$, $R^4$, $R^7$, and $R^8$ are each independently selected from the group consisting of H, F, and OH with the proviso that at least one of $R^2$, $R^3$, $R^4$, $R^7$, and $R^8$ is OH;

$R^{13}$ and $R^{14}$ are each independently selected from the group consisting of H, $R^b$, and $OR^b$;

$R^b$ is $C_{2-7}$ alkyl wherein said alkyl group may be optionally substituted with an $R^c$ group;

$R^c$ is $NR^dR^e$;

or a pharmaceutically acceptable salt or stereoisomer thereof.

6. The compound of claim 5 wherein $R^c$ is $NR^dR^e$;

and $R^d$ and $R^e$ are taken together with the nitrogen atom to which they are attached to form a 6 membered ring, wherein said ring may be optionally interrupted by one of O, NH, $NCH_3$ and S and is optionally substituted with one, two, three or four $C_{1-2}$ alkyl groups, or one or two $R^f$ groups; or a pharmaceutically acceptable salt or stereoisomer thereof.

7. The compound of claim 4 wherein each X is CO; $R^1$, $R^5$, $R^6$, $R^9$, $R^{10}$, $R^{11}$, and $R^{12}$ are H;

$R^2$, $R^3$, $R^4$, $R^7$, and $R^8$ are each independently selected from the group consisting of H, F, and OH with the proviso that at least one of $R^2$, $R^3$, $R^4$, $R^7$, and $R^8$ is OH;

$R^{13}$ and $R^{14}$ are each independently selected from the group consisting of H, $R^b$, and $OR^b$;

$R^b$ is $C_{2-7}$ alkyl wherein said alkyl group may be optionally substituted with an $R^c$ group;

$R^c$ is $NR^dR^e$;

or a pharmaceutically acceptable salt or stereoisomer thereof.

8. The compound of claim 1 wherein one X is $CH_2$ and the other

X is CO;

$R^1$, $R^5$, $R^6$, $R^9$, $R^{10}$, $R^{11}$, and $R^{12}$ are H;

$R^2$, $R^3$, $R^4$, $R^7$, and $R^8$ are each independently selected from the group consisting of H, F, and OH with the proviso that at least one of $R^2$, $R^3$, $R^4$, $R^7$, and $R^8$ is OH;

$R^{13}$ and $R^{14}$ are each independently selected from the group consisting of H, $R^b$, and $OR^b$;

$R^b$ is $C_{2-7}$ alkyl wherein said alkyl group may be optionally substituted with an $R^c$ group;

$R^c$ is $NR^dR^e$;

or a pharmaceutically acceptable salt or stereoisomer thereof.

9. The compound of claim 5 selected from the group consisting of:

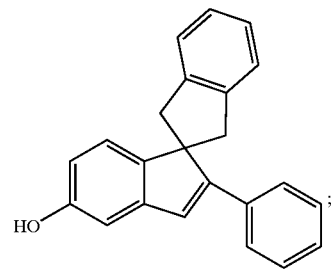

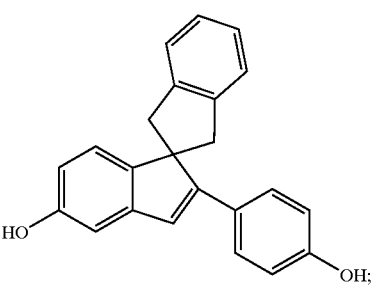

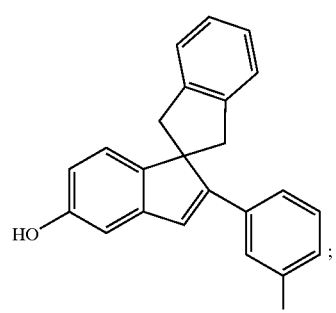

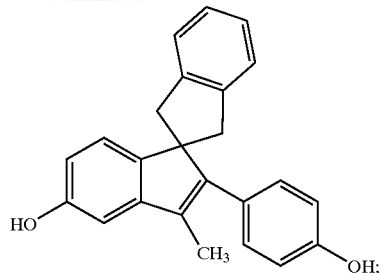

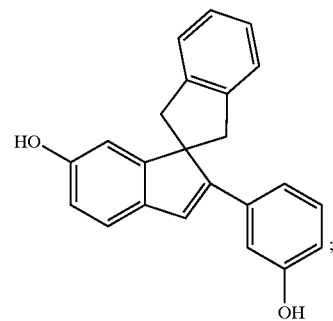

or a pharmaceutically acceptable salt or stereoisomer thereof.

10. The compound of claim 6 selected from the group consisting

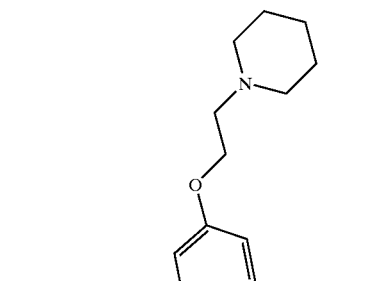

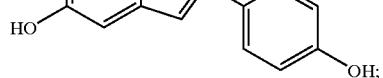
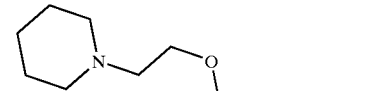

or a pharmaceutically acceptable salt or stereoisomer thereof.

11. The compound according to claim 7 selected from the group consisting of

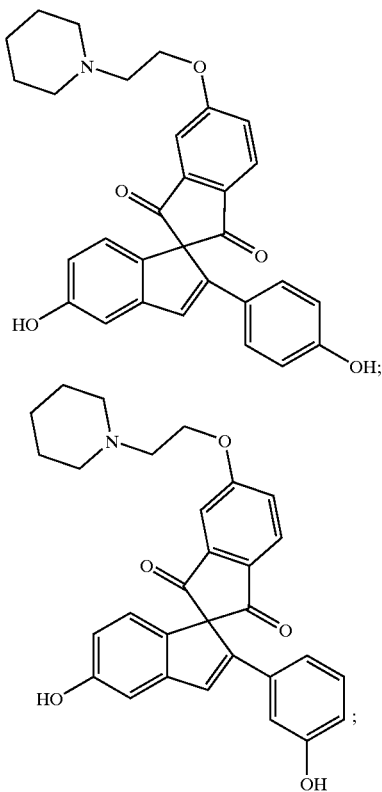

or a pharmaceutically acceptable salt or stereoisomer thereof.

12. The compound of claim 8 selected from the group consisting of:

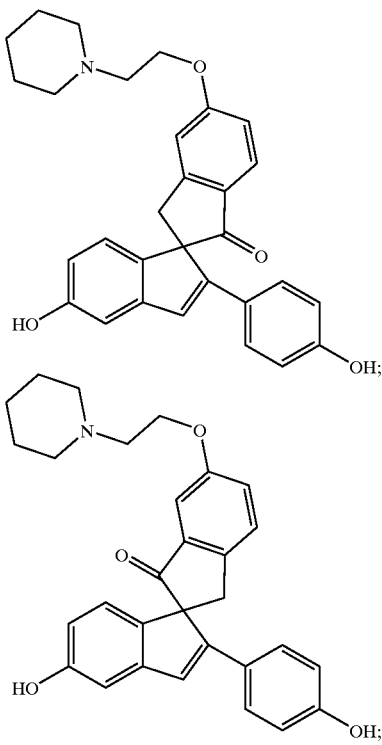

or a pharmaceutically acceptable salt or stereoisomer thereof.

13. A pharmaceutical composition comprising a compound according to claim 1 and a pharmaceutically acceptable carrier.

14. A pharmaceutical composition made by combining a compound according to claim 1 and a pharmaceutically acceptable carrier.

15. A process for making a pharmaceutical composition comprising combining a compound according to claim 1 and a pharmaceutically acceptable carrier.

16. A method of eliciting an estrogen receptor modulating effect in a mammal in need thereof, comprising administering to the mammal a therapeutically effective amount of a compound according to claim 1.

17. The method according to claim 16 wherein the estrogen receptor modulation effect is an estrogen receptor agonizing effect.

18. The method according to claim 17 wherein the estrogen receptor agonizing effect is an ERα receptor agonizing effect.

19. A method of treating a disease in a mammal in need thereof by administering to the mammal a therapeutically effective amount of a compound according to claim 1, wherein said disease is selected from: bone loss, bone fractures, osteoporosis, glucocorticoid induced osteoporosis, Paget's disease, abnormally increased bone turnover, periodontal disease, tooth loss, rheumatoid arthritis, osteoarthritis, periprosthetic osteolysis, osteogenesis imperfecta, metastatic bone disease, hypercalcemia of malignancy, multiple myeloma, cartilage degeneration, endometriosis, uterine fibroid disease, breast cancer, uterine cancer, prostate cancer, hot flashes, cardiovascular disease, impairment of cognitive function, cerebral degenerative disorders, restenosis, gynecomastia, vascular smooth muscle cell proliferation, obesity or incontinence.

20. The method of claim 19 wherein the disease is osteoporosis.

21. The method of claim 19 wherein the disease is metastatic bone disease.

22. A method of treating an estrogen dependent cancer in a mammal in need thereof by administering to the mammal a therapeutically effective amount of a compound according to claim 1.

23. A pharmaceutical composition comprising a compound of claim 1 and another agent selected from: an organic bisphosphonate; a cathepsin K inhibitor; an estrogen; an estrogen receptor modulator; an androgen receptor modulator; an inhibitor of osteoclast proton ATPase; an inhibitor of HMG-CoA reductase; an integrin receptor antagonist; an osteoblast anabolic agent; calcitonin; Vitamin D; a synthetic Vitamin D analogue; or a selective serotonin reuptake inhibitor; or a pharmaceutically acceptable salt or mixture thereof.

24. A method of treating osteoporosis comprising administering to a mammal in need thereof a compound of claim 1 and another agent selected from: an organic bisphosphonate; a cathepsin K inhibitor; an estrogen; an estrogen receptor modulator; an androgen receptor modulator; an inhibitor of osteoclast proton ATPase; an inhibitor of HMG-CoA reductase; an integrin receptor antagonist; an osteoblast anabolic agent; calcitonin; Vitamin D; a synthetic Vitamin D analogue; or a selective serotonin reuptake inhibitor; or a pharmaceutically acceptable salt or mixture thereof.

25. A method of treating bone loss comprising administering to a mammal in need thereof a compound of claim 1 and another agent selected from: an organic bisphosphonate;

a cathepsin K inhibitor; an estrogen; an estrogen receptor modulator; an androgen receptor modulator; an inhibitor of osteoclast proton ATPase; an inhibitor of HMG-CoA reductase; an integrin receptor antagonist; an osteoblast anabolic agent; calcitonin; Vitamin D; a synthetic Vitamin D analogue; or a selective serotonin reuptake inhibitor; or a pharmaceutically acceptable salt or mixture thereof.

26. A method of treating metastatic bone disease comprising administering to a mammal in need thereof a compound of claim 1 and another agent selected from: an organic bisphosphonate; a cathepsin K inhibitor; an estrogen; an estrogen receptor modulator; an androgen receptor modulator; an inhibitor of osteoclast proton ATPase; an inhibitor of HMG-CoA reductase; an integrin receptor antagonist; an osteoblast anabolic agent; calcitonin; Vitamin D; a synthetic Vitamin D analogue; or a selective serotonin reuptake inhibitor; or a pharmaceutically acceptable salt or mixture thereof.

27. A method of lowering cholesterol comprising administering to a mammal in need thereof a compound of claim 1 and another agent selected from: an organic bisphosphonate; a cathepsin K inhibitor; an estrogen; an estrogen receptor modulator; an androgen receptor modulator; an inhibitor of osteoclast proton ATPase; an inhibitor of HMG-CoA reductase; an integrin receptor antagonist; an osteoblast anabolic agent; calcitonin; Vitamin D; a synthetic Vitamin D analogue; or a selective serotonin reuptake inhibitor; or a pharmaceutically acceptable salt or mixture thereof.

* * * * *